(12) United States Patent
Matsumura et al.

(10) Patent No.: US 10,690,665 B2
(45) Date of Patent: *Jun. 23, 2020

(54) MARKER, IMMUNOASSAY METHOD, IMMUNOASSAY REAGENT, METHOD FOR ASSAYING ANALYTE, ANALYTE MEASUREMENT KIT, AND LATERAL-FLOW CHROMATOGRAPHIC TEST STRIP

(71) Applicant: NIPPON STEEL Chemical & Material Co., Ltd., Tokyo (JP)

(72) Inventors: Yasufumi Matsumura, Tokyo (JP); Yasushi Enomoto, Tokyo (JP); Ryuzo Shinta, Tokyo (JP)

(73) Assignee: NIPPON STEEL Chemical & Materials Co., Ltd., Tokyo (JP)

( * ) Notice: Subject to any disclaimer, the term of this patent is extended or adjusted under 35 U.S.C. 154(b) by 26 days.

This patent is subject to a terminal disclaimer.

(21) Appl. No.: 15/323,102

(22) PCT Filed: Jun. 30, 2015

(86) PCT No.: PCT/JP2015/068759
§ 371 (c)(1),
(2) Date: Dec. 30, 2016

(87) PCT Pub. No.: WO2016/002743
PCT Pub. Date: Jan. 7, 2016

(65) Prior Publication Data
US 2017/0168049 A1  Jun. 15, 2017

(30) Foreign Application Priority Data

Jul. 1, 2014  (JP) .................................. 2014-136356
Jul. 1, 2014  (JP) .................................. 2014-136357

(51) Int. Cl.
*G01N 33/558* (2006.01)
*G01N 33/543* (2006.01)
*G01N 33/553* (2006.01)

(52) U.S. Cl.
CPC ..... *G01N 33/558* (2013.01); *G01N 33/54346* (2013.01); *G01N 33/553* (2013.01)

(58) Field of Classification Search
CPC ........... G01N 33/54346; G01N 33/553; G01N 33/558; G01N 33/5581
See application file for complete search history.

(56) References Cited

U.S. PATENT DOCUMENTS

| 5,710,005 A * | 1/1998 | Rittenburg | G01N 33/54386 422/402 |
| 2006/0188932 A1 | 8/2006 | Oka et al. | |
| 2012/0329935 A1 * | 12/2012 | Matsumura | C09D 5/32 524/434 |
| 2013/0224120 A1 | 8/2013 | Amiji et al. | |
| 2017/0219574 A1 * | 8/2017 | Matsumura | C08K 3/08 |
| 2018/0209965 A1 * | 7/2018 | Matsumura | G01N 33/543 |

FOREIGN PATENT DOCUMENTS

| CN | 102253202 | 11/2011 |
| EP | 2674744 | 12/2013 |
| JP | H03-206959 | 9/1991 |
| JP | H05-010950 | 1/1993 |
| JP | 2004163421 | 6/2004 |
| JP | 2006115716 | 5/2006 |
| JP | 2007521460 | 8/2007 |
| JP | 2007225576 | 9/2007 |
| JP | 2009168495 | 7/2009 |
| JP | 2009192270 | 8/2009 |
| JP | 2009210411 | 9/2009 |
| JP | 2011117906 | 6/2011 |
| JP | 2012242277 | 12/2012 |
| JP | 2013522653 | 6/2013 |
| JP | 6353534 | 7/2018 |
| WO | 9964864 | 12/1999 |
| WO | 02092631 | 11/2002 |
| WO | 2005017525 | 2/2005 |

(Continued)

OTHER PUBLICATIONS

Kanahara et al., "Fabrication of gold nanoparticle-polymer composite particles with raspberry, core-shell and amorphous morphologies at room temperature via electrostatic interactions and diffusion," Soft Matter, Jan. 14, 2014, vol. 10, issue 2, pp. 275-280; first published on Oct. 11, 2013.*
Supplementary Information of Kanahara et al., "Fabrication of gold nanoparticle-polymer composite particles with raspberry, core-shell and amorphous morphologies at room temperature via electrostatic interactions and diffusion," Soft Matter, Jan. 14, 2014, vol. 10, issue 2, pp. 275-280; first published on Oct. 11, 2013.*
Rayavarapu et al., "Synthesis and bioconjugation of gold nanoparticles as potential molecular probes for light-based imaging techniques," Int. J. Biomed. Imaging, 2007, vol. 2007, Article ID29817, 10 pages.*

(Continued)

*Primary Examiner* — Galina M. Yakovleva
(74) *Attorney, Agent, or Firm* — JCIPRNET

(57) ABSTRACT

A resin-metal composite 100 to be used as a marker in an immunoassay, said resin-metal composite 100 comprising a resin particle 10 and metal particles 20 and having the following constitution (A) or constitution (B): (A) the average particle size of the resin-metal composite exceeding 300 nm; or (B) the average particle size of the metal particles being in the range of more than 20 nm and less than 70 nm. It is preferred that a part of the metal particles 20 are two- or three-dimensionally distributed in the surface layer part 60 of the resin particle 10, a part of the three-dimensionally distributed metal particles 20 are partly exposed to the outside of the resin particle 10, and a part of the remainder particles are enclosed in the resin particle 10.

8 Claims, 3 Drawing Sheets

(56) References Cited

FOREIGN PATENT DOCUMENTS

WO    2011119822    9/2011

OTHER PUBLICATIONS

Akamatsu et al., "Synthesis of pH-Responsive Nanocomposite Microgels with Size-Controlled Gold Nanoparticles from Ion-Doped, Lightly Cross-Linked Poly(vinylpyridine)," Langmuir, 2010, vol. 26, No. 2, pp. 1254-1259.*
"Office Action of China Counterpart Application," dated Mar. 29, 2018, with English translation thereof, pp. 1-22.
"Office Action of Japan Counterpart Application," with machine English translation thereof, dated Jan. 16, 2018, p. 1-p. 6.
"Search Report of Europe Counterpart Application", dated Oct. 26, 2017, p. 1-p. 7.
"International Search Report (Form PCT/ISA/210)", dated Sep. 15, 2015, with English translation thereof, pp. 1-4, PCT/JP2015/068759.
"Office Action of Japan Counterpart Application," dated Dec. 18, 2018, with English translation thereof, pp. 1-6.
"Office Action of Europe Counterpart Application", dated Jan. 31, 2019, p. 1-p. 4.
Tamao Ishida, et al., "Direct deposition of gold nanoparticles onto polymer beads and glucose oxidation with H2O2," Journal of Colloid and Interface Science, vol. 323, Issue 1, Jul. 1, 2008, pp. 105-111.
"Office Action of China Counterpart Application," with English translation thereof, dated Nov. 12, 2018, p. 1-p. 29.
"Rejection Decision of China Counterpart Application," with machine English translation thereof, dated Jul. 1, 2019, p. 1-p. 24.
"Office Action of Japan Counterpart Application," with English translation thereof, dated Jul. 31, 2019, p. 1-p. 4.
"Office Action of Taiwan Counterpart Application" with English translation thereof, dated Feb. 4, 2020, p. 1-p. 13.
"Search Report of Europe Counterpart Application", dated Mar. 26, 2020, p. 1-p. 7.
"Office Action of China Counterpart Application", dated Mar. 31, 2020, with English translation thereof, p. 1-p. 27.

* cited by examiner

MARKER, IMMUNOASSAY METHOD, IMMUNOASSAY REAGENT, METHOD FOR ASSAYING ANALYTE, ANALYTE MEASUREMENT KIT, AND LATERAL-FLOW CHROMATOGRAPHIC TEST STRIP

CROSS-REFERENCE TO RELATED APPLICATION

This application is a 371 application of the international PCT application serial no. PCT/JP2015/068759, filed on Jun. 30, 2015, which claims the priority benefit of Japan application no. 2014-136357, filed on Jul. 1, 2014, and Japan application no. 2014-136356, filed on Jul. 1, 2014. The entirety of each of the abovementioned patent applications is hereby incorporated by reference herein and made a part of this specification.

BACKGROUND OF THE INVENTION

1. Field of the Invention

The present invention relates to a maker applicable to immunoassay and having excellent sensitivity, durability and visual recognizability and an immunoassay method, an immunoassay reagent, a method for measuring analyte, an analyte measurement kit and a lateral-flow chromatographic test strip utilizing the same.

2. Description of Related Art

Innumerable chemical substances exist in an organism, so the qualitative and quantitative analysis of specific trace components in the organism is an extremely important technique. In fields, such as medical care, pharmacy, health food, biotechnology and environment, drugs and food having effects only on specific parts (chemical substances) in organisms, analysis devices and diagnostic drugs and the like detecting slight changes in organisms develop along with the technique.

One of the analysis techniques is immunoassay. This technique is also called immunological assay, which is a method that qualitatively and quantitatively analyzes trace components by utilizing antigen-antibody specific reaction as one of immunoreactions. Because of high sensitivity or reaction selectivity, the antigen-antibody reaction is widely applied in the fields. Various assay methods exist in immunoassay according to assay principles. Examples are listed as follows: enzyme immunoassay (EIA), radioimmunoassay (RIA), chemiluminescent immunoassay (CLIA), fluorescence immunoassay (FIA), agglutination of latex and so pn (latex immunoassay (LIA), particle agglutination (PA)), immunochromatography (ICA), hemagglutination (HA) and hemagglutination inhibition (HI). Moreover, besides immunoassay, there are physical and chemical assays, biological assay and so on.

Immunoassay qualitatively or quantitatively assays an antigen or an antibody according to change in the reaction between the antigen and the antibody for forming the composite (concentration change of the antigen, the antibody or a composite). When these are assayed, the antibody, the antigen or the composite are bound with a marker, and thereby assay sensitivity is increased.

Therefore, it can be said that the marking capability of the marker is a significant factor affecting assay capability in immunoassay. In the foregoing illustrated immunoassays, erythrocytes (the case of HA), latex particles (the case of LIA), fluorochromes (the case of FIA), radioactive elements (the case of RIA), enzymes (the case of EIA) and chemiluminescent substances (the case of CLIA) and so on can be adopted as markers.

However, when colored microparticles are used as a marker, assay can be determined visually without using a special analysis device, so it can be expected that simpler assay may be realized. As such colored microparticles, examples are listed as follows: colloidal particles of metals and metal oxides and latex particles colored by utilizing a pigment (patent document 1, patent document 4, etc.).

However, because the color of the colloidal particles is determined according to particle sizes and preparation conditions, there exists a problem that it is hard to obtain a desired bright rich color, that is, visual recognizability is insufficient.

In addition, the colored latex particles have the problem of low coloring effect of the utilized pigment and insufficient visual determinability. Furthermore, if the coloring amount of the pigment is increased in order to solve the problem, then the pigment covers the surface of the latex, the original surface state of the latex particles is impaired, and as a result, there exists a problem that it is hard to bind the antigen or the antibody. In addition, there also exists the following problems: blockage in pores of a chromatographic medium such as a membrane filter, or nonspecific agglutination produced by the latex particles or uncertain association between rich coloration resulting from the increase in the coloring amount of the pigment and an increase in performance.

In order to improve the visual recognizability of the marker, following immunochromatography is disclosed: after an antibody (marked antibody) bound with a marker react with an antigen to form a composite, other metals modify the marker, and thereby the assay sensitivity of the marker is increased (patent document 2 and patent document 5). However, in the method, a special device is needed in order to modify metal silver. As a result, operation is complex, and it is hard to achieve a stable increase. In addition, it is considered that assay cost is consumed due to the fact that a special device is required, so applicable purposes and application environment are limited.

In addition, a coloring latex containing gold nanoparticles bound with the surfaces of polymeric latex particles (patent document 3) is disclosed. By binding the surfaces of the polymeric latex particles with the gold nanoparticles, the gold nanoparticles as colorant itself can help to increase visual determinability or assay sensitivity. On the other hand, the gold nanoparticles itself are excellent for the binding of an antigen or an antibody, so, even if the gold nanoparticles are bound until a degree of sufficiently rich color, an enough amount of antigen or antibody can be bound.

γ rays irradiate a dispersion of styrene-acrylic acid copolymer latex and a precursor of gold nanoparticles (i.e. HAuCl), so that the surface of the latex is bound with the gold nanoparticles, and thereby the coloring latex is formed. However, since the gold nanoparticles are only bound with the surface of the latex, not only is the quantity of carried gold particles manifesting surface plasmon absorption limited, but also the gold nanoparticles can easily come off. As a result, the visual recognizability or sensitivity of it as an immunoassay reagent may not be sufficient. In addition, because of the irradiation of electromagnetic radioactive rays such as γ rays, the latex may be injured. Further, although the description of patent document 3 discloses preferred ranges of latex size or gold nanoparticle size, whether it has been verified in these preferred ranges in the embodiments is not clear, so a specified basis of preferred ranges does not exist.

In addition, patent document 4 discloses a metal gold-coated polymer latex particle, and suggests the application of a reagent applicable to microscopic examination and immunoassay.

However, the material or particle size of the metal gold-coated polymer latex particle is not disclosed. Further, the effect of it as a reagent applicable to immunoassay has not been verified. Therefore, the effect of it as a reagent in metal gold and polymer latex particles is not clear.

According to what is mentioned above, although the latex particle bound or coated with the gold nanoparticle is expected as an immunoassay reagent, in the prior art, durability or visual recognizability is not sufficient. In addition, even if visual recognizability is high, applicable purposes and application environment are limited.

DOCUMENTS OF THE PRIOR ART

Patent Documents

Patent Document 1: Japanese Unexamined Patent Application Publication No. Hei-5-10950
Patent Document 2: Japanese Unexamined Patent Application Publication No. 2011-117906
Patent Document 3: Japanese Unexamined Patent Application Publication No. 2009-168495
Patent Document 4: Japanese Unexamined Patent Application Publication No. Hei-3-206959
Patent Document 5: Japanese Unexamined Patent Application Publication No. 2009-192270

SUMMARY OF THE INVENTION

Problem to be Solved by the Invention

The present invention is directed to provide a marker which is applicable to immunoassay, has excellent sensitivity, durability and visual recognizability and can realize high-sensitivity determination without requiring the addition of a special device or operation steps.

Means for Solving the Problem

As the result of the research effort of the inventor and the others, it is discovered that a resin-metal composite with a specific structure can be utilized to solve the problem, and thereby the present invention is achieved.

That is, the marker of the present invention comprises the resin-metal composite with the structure formed by immobilizing metal particles on a resin particle, and is characterized by having any one of the following constitution (A) and constitution (B):

(A) the average particle size of the resin-metal composite exceeding 300 nm; or (B) the average particle size of the metal particles being in a range of more than 20 nm and less than 70 nm.

If the marker of the present invention is in (A), the average particle size of the metal particles can be in a range from 1 nm to 80 nm.

If the marker of the present invention is in (A), the average particle size of the resin-metal composite can be in a range from more than 300 nm to 1000 nm. In this case, the metal particles can be gold particles.

If the marker of the present invention is in (B), the average particle size of the resin-metal composite can be in a range of 100 nm to 1000 nm. In this case, the metal particles can be gold particles.

The marker of the present invention can be prepared by dispersing the resin-metal composite into water.

The marker of the present invention can be used in adsorbing an antigen or an antibody on the surface of the resin-metal composite.

An immunoassay method of the present invention is characterized by using any one of the markers.

An immunoassay reagent in the present invention comprises any one of the markers.

A method for measuring analyte in the present invention is a method for measuring analyte which can assay or quantify an analyte contained in a sample.

The method for measuring analyte in the present invention uses a lateral-flow chromatographic test strip which comprises a membrane and a determination portion formed by immobilizing capturing ligands specifically bound with the analyte on the membrane.

Moreover, the method for measuring analyte in the present invention is characterized by carrying out steps including Step (I) to Step (III) hereinafter:

Step (I): Step of making the analyte contained in the sample contact with a marked antibody formed by utilizing any one of the markers to mark an antibody specifically bound with the analyte.

Step (II): Step of making the composite containing the analyte and the marked antibody formed in Step (I) contact with the capturing ligands in the determination portion.

Step (III): Step of determining colored intensity derived from the localized surface plasmon resonance of the resin-metal composite in the marker.

An analyte measurement kit in the present invention is an analyte measurement kit which uses the lateral-flow chromatographic test strip and is used to assay or quantify an analyte contained in a sample.

The analyte measurement kit in the present invention comprises: a lateral-flow chromatographic test strip, comprising a membrane and a determination portion formed by immobilizing capturing ligands specifically bound with the analyte on the membrane; and an assay reagent, containing a marked antibody formed by utilizing any one of the marker to mark an antibody specifically bound with the analyte.

A lateral-flow chromatographic test strip in the present invention is a lateral-flow chromatographic test strip which is used to assay or quantify an analyte contained in a sample.

The lateral-flow chromatographic test strip in the present invention comprises:

a membrane;

a determination portion, formed by immobilizing capturing ligands specifically bound with the analyte on the membrane in the spreading direction of a sample; and a reaction portion, comprising an marked antibody formed by utilizing any one of the marker to mark an antibody specifically bound with the analyte further upstream than the determination portion.

Effects of the Present Invention

The marker of the present invention is provided with the resin-metal composite with the structure formed by immobilizing the metal particles on the resin particle. Therefore, the quantity of the carried metal particles manifesting localized surface plasmon absorption on the resin particle is high.

Therefore, the marker of the present invention as an excellent material having excellent durability and visual recognizability and capable of realizing high-sensitivity determination without requiring the addition of a special device or operation steps can be preferably applied in immunoassay, such as EIA, RIA, CLIA, FIA, LIA, PA, ICA, HA and HI.

DESCRIPTION OF THE EMBODIMENTS

In reference to the drawings, the embodiments of the present invention are elaborated hereinafter.

First Embodiment

Figure 1:
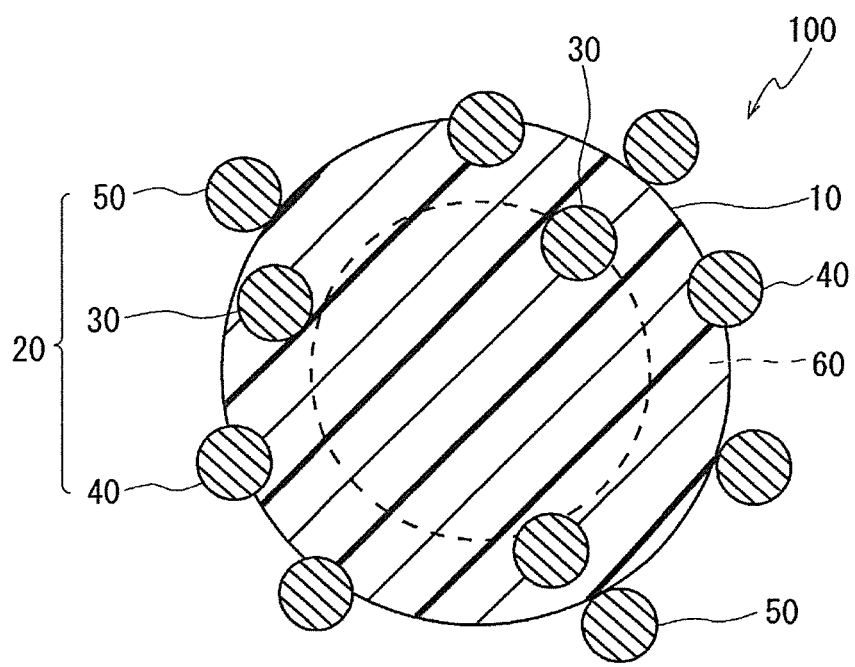
FIG. 1 is a structural schematic diagram representing the section of a resin-metal composite composing a marker in an embodiment of the present invention.

A marker of the first embodiment of the present invention is provided with a resin-metal composite with a structure formed by immobilizing metal particles on a resin particle, and the average particle size of the resin-metal composite exceeds 300 nm. FIG. 1 is a schematic diagram of the section of the resin-metal composite composing the marker of the present embodiment. The resin-metal composite 100 is provided with the resin particles 10 and the metal particles 20. For example, the marker of the present embodiment which is provided with the resin-metal composite 100 can be preferably used as an immunoassay reagent or a material therefor.

In the resin-metal composite 100, the metal particles 20 are dispersed or immobilized on the resin particle 10. In addition, portions of the metal particles 20 of the resin-metal composite 100 are two- or three-dimensionally distributed in a surface layer part 60 of the resin particle 10, moreover, portions of the three-dimensionally distributed metal particles 20 are partially exposed from the resin particle 10, and the rest portions are encased in the resin particle 10.

Here, metal particles completely encased in the resin particle 10 (also called "encased metal particles 30" hereinafter), metal particles having a portion embedded in the resin particle 10 and a portion exposed from the resin particle 10 (also called "partially exposed metal particles 40" hereinafter) and metal particles adsorbed on the surface of the resin particle 10 (also called "surface-adsorbed metal particles 50" hereinafter) exist among the metal particles 20.

When the resin-metal composite 100 is used as the marker, an antibody or an antigen is immobilized on the partially exposed metal particles 40 or the surface-adsorbed metal particles 50 for use. At this point, the antibody or the antigen is immobilized on the partially exposed metal particles 40 and the surface-adsorbed metal particles 50, but, on the other hand, is not immobilized on the encased metal particles 30. However, because the metal particles 20 including the encased metal particles 30 all manifest localized surface plasmon absorption, not only can the partially exposed metal particles 40 and the surface-adsorbed metal particles 50 help to increase the visual recognizability of the marker, but also the encased metal particles 30 can help to increase the visual recognizability of the marker. Further, compared with the surface-adsorbed metal particles 50, the partially exposed metal particles 40 and the encased metal particles 30 have large contact area with the resin particle 10, and, besides, can hardly come off from the resin particle 10 due to the high adsorption force of physics such as anchoring effect produced by the embedded state. Therefore, the durability and stability of the marker using the resin-metal composite 100 can become excellent.

The whole surface of each encased metal particle 30 is covered by resin forming the resin particle 10. In addition, 5 percent to less than 100 percent of the surface area of each partially exposed metal particle 40 is covered by the resin forming the resin particle 10. From the point of durability, the lower limit is preferably 20 percent or more of the surface area, more preferably 30 percent or more. In addition, more than 0 percent but less than 5 percent of the surface area of each surface-adsorbed metal particle 50 is covered by the resin forming the resin particle 10.

In addition, relative to the weight of the resin-metal composite 100, the quantity of the carried metal particles 20 (the total of the encased metal particles 30, the partially exposed metal particles 40 and the surface-adsorbed metal particles 50) of the resin-metal composite 100 is preferably 5 wt % (percentage by weight) to 70 wt %. If it is in the range, then the visual recognizability, visual determinability and assay sensitivity of the resin-metal composite 100 as the marker are excellent. If the quantity of the carried metal particles 20 is less than 5 wt %, then there exists a tendency of decrease in the amount of the immobilized antibody or antigen and decrease in assay sensitivity. The quantity of the carried metal particles 20 is more preferably 15 wt % to 70 wt %.

In addition, preferably, 10 wt % to 90 wt % of the metal particles 20 are the partially exposed metal particles 40 and the surface-adsorbed metal particles 50. If it is in the range, then the amount of the antibody or the antigen immobilized onto the metal particles 20 can be sufficiently guaranteed, so the sensitivity of it as the marker is high. More preferably, 20 wt % to 80 wt % of the metal particles 20 are the partially exposed metal particles 40 and the surface-adsorbed metal particles 50, and from the point of durability, more preferably, the surface-adsorbed metal particles 50 are 20 wt % or less.

In addition, in order to obtain excellent assay sensitivity in immunoassay, preferably 60 wt % to 100 wt %, preferably 75 wt % to 100 wt % or more preferably 85 wt % to 100 wt % of the metal particles 20 exist in the surface layer part 60, and, more preferably, exist in a range of 40% of particle radius in a depth direction from the surface of the resin particle 10. In addition, 5 wt % to 90 wt % of the metal particles 20 existing in the surface layer part 60 are the partially exposed metal particles 40 or the surface-adsorbed metal particles 50, sufficiently guaranteeing the amount of the antibody or the antigen immobilized onto the metal particle 20, so the sensitivity of it as the marker is high as preferred. In other words, 10 wt % to 95 wt % of the metal particles 20 existing in the surface layer part 60 can be the encased metal particles 30.

Here, the "surface layer part" means a range of 50% of the particle radius in the depth direction from the surface of the resin particle 10 with the outermost position (i.e. the protruding ends of the partially exposed metal particles 40 or the surface-adsorbed metal particles 50) of the resin-metal composite 100 as a datum. In addition, "two-dimensionally distributed" means that the metal particles 20 are distributed in the surface direction of the resin particle 10. "three-dimensionally distributed" means that the metal particles 20 are distributed not only in the surface direction of the resin particle 10 but also in the depth direction. From the point of the metal particles 20 hard to come off from the resin particle 10 and the point of the amount of the carried metal particles 20 becoming larger, it is preferred that the metal particles 20 are "three-dimensionally distributed".

In addition, in the present embodiment, the average particle size of the resin-metal composite 100 exceeds 300 nm. If the average particle size of the resin-metal composite 100 is 300 nm or less, then there exists a tendency of decrease in the visual recognizability or sensitivity of the marker. The average particle size of the resin-metal composite 100 is preferably of more than 300 nm to 1000 nm, more preferably of 340 nm to less than 650 nm. Here, the particle size of the resin-metal composite 100 means a value which is obtained by adding the particle size of the resin particle 10 with the length of the protruding portions of the partially exposed metal particles 40 or the surface-adsorbed metal particles 50, and can be determined by a laser diffraction/scattering method, a dynamic light scattering method or a centrifugal precipitation method.

Preferably the resin particle 10 is a polymer particle which is provided with a substituent group capable of adsorbing metal ions in the structure. In particular, a nitrogenous polymer particle is preferred. Nitrogen atoms in a nitrogenous polymer can easily chemically adsorb the precursor (i.e. anionic metal ions) of a metal particle, such as gold or palladium, which has excellent visual recognizability and can easily immobilize an antigen or an antibody, so it is preferred. In the present embodiment, the metal ions adsorbed in the nitrogenous polymer are reduced, so that metal nanoparticles are formed, so portions of the produced metal particles 20 become the encased metal particles 30 or the partially exposed metal particles 40. In addition, because carboxylic acid and the like can adsorb cationic metal ions like acrylic acid polymer, the precursor of a metal particle, such as silver, nickel or copper (i.e. cationic metal ions), can be easily adsorbed, so that the metal particles 20 of silver, nickel, copper or the like can be formed, and an alloy of a metal, such as gold or palladium, can be made.

On the other hand, in the case that it is a resin particle rather than the nitrogenous polymer having the substituent group capable of adsorbing metal ions in the structure, for example, in the case of polystyrene, the metal ions can hardly be adsorbed in resin. As a result, the majority of the produced metal particles 20 are the surface-adsorbed metal particles 50. As mentioned above, the contact area between the surface-adsorbed metal particles 50 and the resin particle 10 is small, so there exists a tendency of low bonding force between the resin and the metal and great affection of the metal particles 20 coming off from the resin particle 10.

The nitrogenous polymer is resin which has nitrogen ions on the main chain or the side chain, for example, polyamine, polyamide, polypeptide, polyurethane, polyurea, polyimide, polyimidazole, polyoxazole, polypyrrole or polyaniline. Among these, polyamine, such as poly-2-vinylpyridine, poly-3-vinylpyridine or poly-4-vinylpyridine, is preferred. In addition, for example, when there are nitrogen atoms on the side chain, acrylic resin, phenolic resin and epoxy resin can be widely utilized.

For example, the metal particles 20 can apply silver, nickel, copper, gold and palladium. Gold and palladium which have excellent visual recognizability and can easily immobilize an antigen or an antibody are preferred. These manifest absorption stemming from localized surface plasmon resonance, and therefore are preferred. Gold with good stability in storage is more preferred. These metals can be used as monomers or composites such as alloys. Here, for example, gold alloy means an alloy which contains gold and metal varieties except gold, and contains 10 wt % or more of gold.

In addition, for example, the average particle size of the metal particles 20 relaying on scanning electron microscope (SEM) observation to determine length is preferably 1 nm to 80 nm. In the case that the average particle size of the metal particles 20 is less than 1 nm or exceeds 80 nm, a localized surface plasmon can hardly manifest, so there exists a tendency of decrease in sensitivity. When the metal particles 20 are gold particles, the average particle size of the metal particles 20 in the first embodiment is preferably of 20 nm to less than 70 nm, more preferably of 22 nm to less than 50 nm.

Second Embodiment

A marker of the second embodiment of the present invention is provided with a resin-metal composite with a structure formed by immobilizing metal particles on a resin particle, and the average particle size of the metal particles is in a range of more than 20 nm and less than 70 nm. Except the range of the average particle size of the metal particles and the range of the average particle size of the resin-metal composite that are different from that of the resin-metal composite 100 of the first embodiment (FIG. 1), the resin-metal composite composing a marker of the present embodiment is the same as the resin-metal composite 100 of the first embodiment (FIG. 1). In reference to FIG. 1, the differences from the first embodiment are described as central points hereinafter.

In the resin-metal composite 100 used in the second embodiment, for example, the average particle size of the metal particles 20 depending on scanning electron microscope (SEM) observation to determine length is more than 20 nm and less than 70 nm. If the average particle size of the metal particles 20 is 20 nm or less, then there exists a tendency of decrease in sensitivity; and if it is 70 nm or more, then there exists a tendency of decrease in visual recognizability. More preferably, the average particle size of the metal particles 20 is 22 nm to less than 50 nm.

In addition, for example, the average particle size of the resin-metal composite 100 is preferably 100 nm to 1000 nm. If the average particle size of the resin-metal composite 100 is less than 100 nm, then, for example, when the gold particles are used as the metal particles 20, there exists a tendency that the quantity of the carried gold particles becomes less, and therefore there exists a tendency that coloring becomes weak in comparison with gold particles of the same size; and if the average particle size of the resin-metal composite 100 exceeds 1000 nm, then there exists a tendency of easy blockage in pores of a chromatographic medium, such as a membrane filter, or a tendency of decrease in dispersibility when the resin-metal composite 100 is prepared into a reagent. The average particle size of the resin-metal composite 100 is preferably 100 nm to less than 700 nm, more preferably 340 nm to less than 650 nm. Here, the particle size of the resin-metal composite 100 means a value which is obtained by adding the particle size of the resin particle 10 with the length of the protruding portions of the partially exposed metal particles 40 or the surface-adsorbed metal particles 50, and can be determined by a laser diffraction/scattering method, a dynamic light scattering method or a centrifugal precipitation method.

In the resin-metal composite 100 used in the marker of the second embodiment, the other constitution is the same as that of the resin-metal composite 100 used in the first embodiment, and therefore description is omitted.

[Preparation Method for Resin-Metal Composite]

Preparation methods for the resin-metal composites 100 used in the markers of the first embodiment and the second embodiment are not specially limited. For example, solution containing metal ions is added into dispersion of resin particles 10 prepared by the emulsion polymerization method, so that the metal ions are adsorbed on the resin particles 10 (called "metal ion-adsorbing resin particles hereinafter"). Further, the metal ion-adsorbing resin particles are added into a reducing agent solution, so that the metal ions are reduced to form metal particles 20, and thereby the resin-metal composite 100 is obtained.

In addition, for example, when gold particles are used as the metal particles 20, aqueous chloroauric acid (HAuCl4) solution can be used as the solution containing the metal ions. In addition, a metal complex can be used to substitute for the metal ions.

In addition, as a solvent for the solution containing the metal ions, aqueous alcohol or alcohol, such as methanol, ethanol, n-propyl alcohol, isopropyl alcohol, n-butyl alcohol, sec-butyl alcohol or tert-butyl alcohol, or acid, such as hydrochloric acid, sulfuric acid or nitric acid, can be used to substitute for water.

In addition, if needed, an additive, such as various water-miscible organic solvents (such as water-soluble macromolecular compound (such as polyvinyl alcohol), surfactant, alcohols, ethers (such as tetrahydrofuran, diethyl ether and diisopropyl ether), polyhydric alcohols (such as alkylene glycol, polyalkylene glycol, their monoalkyl ether or dialkyl ether and glycerol) and ketones (such as acetone and methyl ethyl ketone)), can be added into the solution. Such additive accelerates the speed of the reduction reaction of the metal ions, and is also effective in controlling the size of the produced metal particles 20.

In addition, a well-known reducing agent can be used. Examples are listed as follows: sodium borohydride, dimethylamine borane, citric acid, sodium hypophosphite, hydrazine hydrate, hydrazine hydrochloride, hydrazine sulfate, formaldehyde, sucrose, glucose, ascorbic acid, sodium hypophosphite, hydroquinone and Rochelle salt. Sodium borohydride, dimethylamine borane or citric acid is preferred. If needed, surfactant can be added into the reducing agent solution, or the pH of the solution is regulated. The pH can be regulated by a buffering agent (such as boric acid or phosphoric acid), acid (such as hydrochloric acid or sulfuric acid) or alkali (such as sodium hydroxide or potassium hydroxide).

Further, the reduction speed of the metal ions is regulated by the temperature of the reducing agent solution, so that the particle size of the formed metal particles can be controlled.

In addition, when the metal ions in the metal ion-adsorbing resin particles are reduced to produce the metal particles 20, the metal ion-adsorbing resin particles can be added into the reducing agent solution, or the reducing agent can be added into the metal ion-adsorbing resin particles, nevertheless, from the point of the easiness of the production of encased metal particles 30 and partially exposed metal particles 40, the former is preferred.

In addition, in order to keep the dispersibility of the resin-metal composite 100 in water, for example, a dispersing agent, such as citric acid, poly-L-lysine, polyvinylpyrrolidone, polyvinylpyridine, polyvinyl alcohol, disperbyk 194, disperbyk 180 or disperbyk 184 (produced by BYK-Chemie Japan), can be added.

Further, pH can be regulated by a buffering agent (such as boric acid or phosphoric acid), acid (such as hydrochloric acid or sulfuric acid) or alkali (such as sodium hydroxide or potassium hydroxide), and dispersibility is kept.

Particularly, by adsorbing the antigen or antibody on the surfaces of the metal particles 20, the resin-metal composite 100 with the above-mentioned composition is preferably applicable as a marker to immunoassay, such as EIA, RIA, CLIA, FIA, LIA, PA, ICA, HA and HI. In addition, it can be particularly used as a marker with excellent visual determinability in low-concentration regions (high-sensitivity regions). In addition, the form of the marker is not specially limited, for example, it can be used as dispersion which is formed by dispersing the resin-metal composite 100 into water or a pH-regulated buffer.

Methods for adsorbing the antigen or antibody onto the surface of the metal particles 20 are not specially limited, and the well-known physical adsorption and chemical adsorption methods can be utilized. Examples are listed as follows: physical adsorption, such as immersing the resin-metal composite 100 into a buffer containing the antigen or antibody for incubation, or chemical adsorption, such as introducing an SH group into the antigen or antibody to react with the resin-metal composite 100 to form an Au—SH bond. In order to make the bonding between the metal particles 20 and the antigen or antibody become firm, chemical adsorption is preferred.

A method for measuring analyte, a lateral-flow chromatographic test strip and an analyte assay and quantification kit which adopt the resin-metal composite 100 as a marker are then described.

[Lateral-Flow Chromatographic Test Strip]

Figure 2:
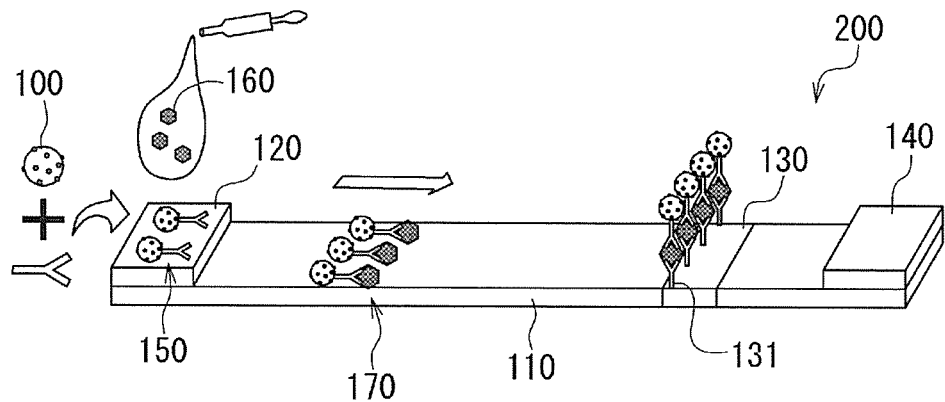
FIG. 2 is an explanatory diagram representing the summary of a method for measuring analyte using a lateral-flow chromatographic test strip in an embodiment of the present invention.

Firstly, in reference to FIG. 2, a lateral-flow chromatographic test strip (test strip) in an embodiment of the present invention is described. As mentioned hereinafter, the test strip 200 can be preferably used in a method for measuring analyte in an embodiment of the present invention.

The test strip 200 is provided with a membrane 110. In the membrane 110, a sample addition portion 120, a determination portion 130 and a liquid-absorbing portion 140 are sequentially arranged in the spreading direction of a sample.

<Membrane>

A material which is used as a membrane in ordinary test strips can be applied as the membrane 110 used in the test strip 200. For example, the membrane 110 is formed by an insert material including the following microporous materials (substances not reacting with an analyte 160 and various ligands, etc), the microporous substances show capillarity, and when added, the sample spreads. Specific examples as the membrane 110 are listed as follows: fibrous or non-woven fibrous matrices and films containing polyurethane, polyester, polyethylene, polyvinyl chloride, polyvinylidene fluoride, nylon and cellulose derivative, etc., filter paper, glass fiber filter paper, cloth and cotton. Among these, preferably, a film containing cellulose derivatives or nylon, filter paper or glass fiber filter paper can be used, or more preferably, a cellulose nitrate film, a mixed nitrocellulose ester (a mixture of cellulose nitrate and cellulose acetate) film, a nylon film or filter paper can be used.

In order to make operation easier, the test strip 200 is preferably a supporting body with the supporting membrane 110. For example, as the supporting body, plastic can be used.

<Sample Addition Portion>

The test strip 200 can also be provided with the sample addition portion 120 for the addition of a sample containing the analyte 160. In the test strip 200, the sample addition portion 120 is a portion for receiving the sample containing the analyte 160. In the spreading direction of the sample, the sample addition portion 120 can be formed on the membrane 110 further upstream than the determination portion 130, or a sample addition pad containing a material, such as cellulose filter paper, glass fibers, polyurethane, polyacetate, cellulose acetate, nylon or cotton, can be arranged on the membrane 110 to form the sample addition portion 120.

<Determination Portion>

Capturing ligands 131 which are specifically bound with the analyte 160 are immobilized in the determination portion 130. As long as the capturing ligands 131 are specifically bound with the analyte 160, there is no special limitation in use, for example, an antibody for the analyte 160 can be preferably used. Even if the sample is supplied to the test strip 200, the capturing ligands 131 are immobilized in a manner of not moving from the determination portion 130. The capturing ligands 131 only need to be directly or indirectly immobilized on the membrane 110 by physical bonding or chemical bonding or adsorption.

In addition, as long as the determination portion 130 is composed like a composite 170 containing a marked antibody 150 and the analyte 160 in contact with the capturing ligands 131 specifically bound with the analyte 160, there is no special limitation. For example, the capturing ligands 131 can be directly immobilized on the membrane 110, or the capturing ligands 131 can be immobilized on a pad containing cellulose filter paper, glass fibers or non-woven cloth fixed on the membrane 110.

<Liquid-Absorbing Portion>

For example, the liquid-absorbing portion 140 can be formed by a pad of water-absorbing material such as cellulose filter paper, non-woven cloth, cloth and cellulose acetate. The moving speed of the sample after the front line of spreading of the added sample arrives at the liquid-absorbing portion 140 is different according to the materials and sizes of the liquid-absorbing portion 140. Therefore, by choosing the material and size of the liquid-absorbing portion 140, the most suitable speed can be set for the assay and quantification of the analyte 160. Moreover, the composition of the liquid-absorbing portion 140 is optional, and therefore can be omitted.

If needed, the test strip 200 can also comprise any portions, such as a reaction portion and a control portion.

<Reaction Portion>

Although graphical representation is omitted, in the test strip 200, the reaction portion containing the marked antibody 150 can be formed on the membrane 110. In the flowing direction of the sample, the reaction portion can be arranged further upstream than the determination portion 130. Furthermore, the sample addition portion 120 in FIG. 2 can be used as the reaction portion. When the test strip 200 has the reaction portion, if the sample containing the analyte 160 is supplied to the reaction portion or the sample addition portion 120, then, in the reaction portion, the analyte 160 contained in the sample can be in contact with the marked antibody 150. In this case, the sample is only supplied to the reaction portion or the sample addition portion 120, so that the composite 170 containing the analyte 160 and the marked antibody 150 can be formed, so a so-called one-step immunochromatography can be implemented.

As long as the reaction portion contains the marked antibody 150 specifically bound with the analyte 160, there is no special limitation, and the reaction portion can be formed by directly applying the marked antibody 150 on the membrane 110. Or the reaction portion can also be formed by immobilizing a pad (conjugate pad) on the membrane 110, wherein the pad containing cellulose filter paper, glass fibers or non-woven cloth and the marked antibody 150 is impregnated in the pad.

<Control Portion>

Although graphical representation is omitted, the control portion can also be formed on the test strip 200 in the spreading direction of the sample by immobilizing the capturing ligands specifically bound with the marked antibody 150 on the membrane 110. By determining colored intensity in the determination portion 130 and the control portion together, it can be determined that the sample supplied to the test strip 200 arrives at the reaction portion and the determination portion 130 after spreading, and examination can be normally carried out. Moreover, except using other types of capturing ligands specifically bound with the marked antibody 150 to replace the capturing ligands 311, the control portion can be made in the same way as the determination portion 130, and can adopt the same composition.

[Method for Measuring Analyte]

A method for assaying the analyte 160 using the test strip 200 in an embodiment of the present invention is then described.

The method for assaying the analyte 160 in the present invention is a method for assaying the analyte 160 which can assay or quantify the analyte 160 contained in the sample. The method for assaying the analyte 160 in the present invention can use the test strip 200 comprising the membrane 110 and the determination portion 130 formed by immobilizing the capturing ligands 131 specifically bound with the analyte 160 on the membrane 110, and comprises Step (I) to Step (III) below:

Step (I): Step of making the analyte 160 contained in the sample contact with the marked antibody 150 formed by utilizing the resin-metal composite 100 having the structure formed by immobilizing the plurality of metal particles 20 on the resin particle 10 to mark an antibody specifically bound with the analyte 160.

Step (II): Step of making the composite containing the analyte 160 and the marked antibody 150 formed in Step (I) contact with the capturing ligands 131 in the determination portion 130.

Step (III): Step of determining colored intensity derived from the localized surface plasmon resonance of the resin-metal composite 100.

Step (I):

Step (I) is a step of making the analyte 160 contained in the sample contact with the marked antibody 150. As long as the composite 170 containing the analyte 160 and the marked antibody 150 is formed, there is no special limitation in the form of contact. For example, the sample can be supplied to the sample addition portion 120 or reaction portion (graphical representation omitted) of the test strip 200 and the analyte 160 is made contact with the marked antibody 150 in the reaction portion, or, before the sample is supplied to the test strip 200, the analyte 160 in the sample can be made contact with the marked antibody 150.

The composite 170 foamed in Step (I) is moved after spreading on the test strip 200, and arrives at the determination portion 130.

Step (II):

Step (II) is a step of making the composite 170 containing the analyte 160 and the marked antibody 150 formed in Step (I) contact with the capturing ligands 131 in the determination portion 130 of the test strip 200. If the composite 170 is made contact with the capturing ligands 131, then the capturing ligands 131 are specifically bound with the analyte 160 of the composite 170. As a result, the composite 170 is captured in the determination portion 130.

Furthermore, because the capturing ligands 131 are not specifically bound with the marked antibody 150, when the marked antibody 150 not bound with the analyte 160 arrives at the determination portion 130, the marked antibody 150 not bound with the analyte 160 passes through the determination portion 130. Here, when the control portion (graphical representation omitted) on which other capturing ligands specifically bound with the marked antibody 150 are immobilized is formed in the test strip 200, the marked antibody 150 which has passed through the determination portion 130 continues to spread, and is bound with the other capturing ligands in the control portion. As a result, the marked antibody 150 which does not form the composite 170 along with the analyte 160 is captured in the control portion.

After Step (II), if needed, before Step (III), for example, a cleaning step of cleaning the test strip 200 by utilizing a buffer commonly used in biochemical examination, such as water, normal saline or phosphate buffer, can be implemented. By means of the cleaning step, the marked antibody 150 (marked antibody 150 not bound with the analyte 160 to form the composite 170) which is not captured in the determination portion 130 or the determination portion 130 and the control portion can be removed.

By implementing the cleaning step, when coloration caused by the localized surface plasmon resonance of the resin-metal composite 100 in the determination portion 130 or the determination portion 130 and the control portion is determined in Step (III), the colored intensity of the background can be decreased, the signal/background ratio can be increased, and assay sensitivity or quantifiability can be further increased.

Step (III):

Step (III) is a step of determining colored intensity derived from the localized surface plasmon resonance of the resin-metal composite 100. After Step (II) or the cleaning step, if needed, is implemented, in the test strip 200, colored intensity derived from the localized surface plasmon resonance of the resin-metal composite 100 is determined.

Moreover, when the control portion is formed in the test strip 200, by means of Step (II), in the control portion, the marked antibody 150 is captured by the other capturing ligands to form the composite. Therefore, in Step (III), in the test strip 200, not only can coloration caused by localized surface plasmon resonance be generated in the determination portion 130, but also coloration caused by localized surface plasmon resonance be generated in the control portion. Thus, by determining colored intensity in the determination portion 130 and the control portion together, whether the sample supplied to the test strip 200 arrives at the reaction portion and the determination portion 130 after spreading normally can be determined.

<Sample and Analyte>

As long as the sample in the method for measuring analyte in the present embodiment contains a substance capable of becoming an antigen, such as protein, as the analyte 160, there is no special limitation. Examples are listed as follows: an organism sample (i.e. whole blood, serum, plasma, urine, saliva, phlegm, rhinal swab fluid or pharyngeal swab fluid, spinal fluid, amniotic fluid, nipple secretion, tear, sweat, extract coming from skin, extract coming from tissues or cells and feces, etc.) containing the target analyte 160 or extract of food. If needed, in order to easily cause the specific binding reaction between both the marked antibody 150 and the capturing ligands 131 and the analyte 160, before Step (I), the analyte 160 contained in the sample is pretreated. Here, as pretreatment, chemical treatment utilizing various chemicals (such as acid, alkali and surfactant) or physical treatment utilizing heating, agitation and ultrasonic waves can be adopted. In particular, when the analyte 160 is a substance normally not exposed to the surface, such as an influenza virus NP antigen, surfactant is preferably utilized for treatment. As the surfactant for this purpose, non-ionic surfactant can be used in consideration of specific binding reaction, such as binding reactivity between ligands for antigen-antibody reaction and the analyte 160.

In addition, the sample can be properly diluted by a solvent (such as water, normal saline or buffer) or a water-miscible organic solvent normally used in immunological analysis.

As the analyte 160, examples are listed as follows: proteins of tumor pointers, signal transmission substances, hormone and so on (including polypeptide, oligopeptide and the like), nucleic acids (including single-stranded or double-stranded deoxyribonucleic acid (DNA), ribonucleic acid (RNA) and polynucleotide, oligonucleotide, peptide nucleic acid (PNA) and the like) or substances with nucleic acid, saccharides (including oligosaccharide, polysaccharides, carbohydrate chain and the like) or substances with carbohydrate chains, and other molecules such as lipid. As long as it can be specifically bound with the marked antibody 150 and the capturing ligands 131, there is no special limitation. Examples are listed as follows: carcino-embryonic antigen (CEA), HER2 protein, prostate specific antigen (PSA), CA19-9, α-fetoprotein (AFP), immunosuppressive acidic protein (IAP), CA15-3, CA125, estrogen receptor, progesterone receptor, fecal occult blood, troponin 1, troponin T, CK-MB, CRP, human chorionic gonadotrophin (HCG), luteinizing hormone (LH), follicle stimulating hormone (FSH), syphilis antibody, influenza virus, human hemoglobin, chlamydia antigen, group A β hemolytic streptococcus antigen, HBs antibody, HBs antigen, rotavirus, adenovirus, albumin and glycated albumin. Among these, antigen which can be dissolved by non-ionic surfactant is preferred, and antigen which is formed from self-aggregate like the nucleoprotein of virus is more preferred.

<Marked Antibody>

The marked antibody 150 is used in Step (I) to contact with the analyte 160 contained in the sample, so that the composite 170 containing the analyte 160 and the marked antibody 150 is formed. The marked antibody 150 is formed by utilizing the resin-metal composite 100 having the structure formed by immobilizing the plurality of metal particles 20 on the resin particle 10 to mark an antibody specifically bound with the analyte 160. Here, the so-called "marking" means directly or indirectly immobilizing the resin-metal composite 100 onto the antibody by chemical binding or physical binding or adsorption on the basis of the degree of the resin-metal composite 100 not coming off from the marked antibody 150 in Step (I) to Step (III). For example, the marked antibody 150 can be formed by directly binding the antibody with the resin-metal composite 100, or can be formed by binding the antibody with the resin-metal composite 100 through any tie molecules or respectively immobilizing them on insoluble particles.

In addition, in the present embodiment, there is no special limitation on "antibody", for example, besides polyclonal antibodies, monoclonal antibodies and antibodies obtained by genetic recombination, antibody fragments (such as H chain, L chain, Fab and F(ab')2) capable of being bound with antigens can be used. In addition, immune globulin can be any one of IgG, IgM, IgA, IgE and IgD. Animal species producing antibodies can be the human being and animals (e.g. mouse, rat, rabbit, goat and horse) except the human being. Specific examples as the antibody are listed as follows: anti-PSA antibody, anti-AFP antibody, anti-CEA antibody, anti-adenovirus antibody, anti-influenza virus antibody, anti-HCV antibody, anti-IgG antibody and anti-human IgE antibody.

<Preferred Preparation Method for Marked Antibody>

A preferred preparation method for the marked antibody 150 is then described. The preparation of the marked antibody 150 can at least comprise Step A below:

Step A: Step of binding the resin-metal composite 100 with the antibody by mixing under a first pH condition to obtain the marked antibody 150, and preferably, Step B is further included;

Step B: Step of treating the marked antibody 150 under a second pH condition.

[Step A]

In Step A, under the first pH condition, the resin-metal composite 100 and the antibody are mixed, so that the marked antibody 150 is obtained. Preferably, in Step A, the solid resin-metal composite 100 contacts with the antibody in the state of being dispersed in the liquid phase. The first pH condition is different according to the metal varieties of the metal particles 20 in the resin-metal composite 100.

When the metal particles 20 of the resin-metal composite 100 are gold particles (including gold alloy particles; the same is true hereinafter), from the point of making the resin-metal composite 100 uniformly contact with the antibody under the state of maintaining the dispersion of the resin-metal composite 100 and the activity of the antibody in order to be bound with the antibody, the first pH condition is preferably a condition of pH in a range from 2 to 7, and further, an acidic condition is more preferred, for example, pH is in a range from 2.5 to 5.5. When the metal particles 20 are gold particles, if the condition in binding the resin-metal composite 100 with the antibody is pH less than 2, then there will exist a situation that the antibody is deteriorated and inactivated due to strong acidity; and if pH exceeds 7, then the resin-metal composite 100 will be aggregated and hardly dispersed when mixed with the antibody. However, when the antibody is not inactivated due to strong acidity, even if pH is less than 2, treatment can still be carried out.

In addition, when the metal particles 20 of the resin-metal composite 100 are particles rather than gold particles, e.g. palladium particles or their alloys, from the point of making the resin-metal composite 100 uniformly contact with the antibody under the state of maintaining the dispersion of the resin-metal composite 100 and the activity of the antibody in order to be bound with the antibody, the first pH condition is preferably a condition of pH in a range from 2 to 10, and more preferably, for example, pH is in a range from 5 to 9. When the metal particles 20 are particles rather than gold particles, if the condition in binding the resin-metal composite 100 with the antibody is pH less than 2, then there will exist a situation that the antibody is deteriorated and inactivated due to strong acidity; and if pH exceeds 10, then the resin-metal composite 100 will be aggregated and hardly dispersed when mixed with the antibody. However, when the antibody is not inactivated due to strong acidity, even if pH is less than 2, treatment can still be carried out.

Preferably, Step A is carried out in binding buffer regulated to the first pH condition. For example, a specified amount of resin-metal composite 100 is mixed in the binding buffer regulated to the pH, and is sufficiently mixed. For example, as the binding buffer, boric acid solution regulated to specified concentration can be used. For example, the pH of the binding buffer can be regulated by using hydrochloric acid, sodium hydroxide, etc.

Afterwards, a specified amount of antibody is added into the obtained mixture, and is sufficiently agitated and mixed, and thereby a marked antibody-containing solution can be obtained. For example, only the marked antibody 150 as solid part is separated out from the marked antibody-containing solution obtained in this way by a solid-liquid separation method, such as centrifugal separation.

[Step B]

In Step B, under the second pH condition, the marked antibody 150 obtained in Step A is treated in order to carry out blockage of inhibiting the non-specific adsorption of the marked antibody 150. In this case, under the second pH condition, the marked antibody 150 which is separated out by the solid-liquid separation method is dispersed in the liquid phase. The condition of blockage is different according to the metal varieties of the metal particles 20 in the resin-metal composite 100.

When the metal particles 20 of the resin-metal composite 100 are gold particles, from the point of keeping the activity of the antibody and inhibiting the aggregation of the marked antibody 150, for example, the second pH condition is preferably pH in a range from 2 to 9, and further, from the point of inhibiting the non-specific adsorption of the marked antibody 150, an acidic condition is more preferred, for example, pH is in a range from 2 to 6. If the condition of blockage is pH less than 2, then there will exist a situation that the antibody is deteriorated and inactivated due to strong acidity; and if pH exceeds 9, then the marked antibody 150 will be aggregated and hardly dispersed.

In addition, when the metal particles 20 of the resin-metal composite 100 are particles rather than gold particles, from the point of keeping the activity of the antibody and inhibiting the aggregation of the marked antibody 150, for example, the second pH condition is preferably pH in a range from 2 to 10, and from the point of inhibiting the non-specific adsorption of the marked antibody 150, more preferably, pH is in a range from 5 to 9. If the condition of blockage is pH less than 2, then there will exist a situation that the antibody is deteriorated and inactivated due to strong acidity; and if pH exceeds 10, then the marked antibody 150 will be aggregated and hardly dispersed.

Preferably, Step B is carried out by using blocking buffer regulated to the second pH condition. For example, the blocking buffer regulated to the pH is added into a specified amount of marked antibody 150, and the marked antibody 150 is uniformly dispersed into the blocking buffer. For example, preferably, as the blocking buffer, a solution of protein not bound with an assayed substance is used. As the protein capable of being used in the blocking buffer, examples are listed as follows: bovine serum albumin, ovalbumin, casein and gelatin. More specifically, preferably, a bovine serum albumin solution regulated to specified concentration is used. For example, the pH of the blocking buffer can be regulated by using hydrochloric acid, sodium hydroxide, etc. Preferably, the marked antibody 150 can be dispersed by using a dispersion method, such as ultrasonic treatment. Dispersion in which the marked antibody 150 is uniformly dispersed is obtained in this way.

Dispersion of the marked antibody 150 can be obtained in this way. For example, only the marked antibody 150 as solid part is separated out from the dispersion by a solid-liquid separation method, such as centrifugal separation. In addition, if needed, cleaning treatment, storage treatment and the like can be implemented. Cleaning treatment and storage treatment are described hereinafter.

(Cleaning Treatment)

Cleaning treatment adds cleaning buffer into the marked antibody 150 separated out by the solid-liquid separation method, and uniformly disperses the marked antibody 150 into the cleaning buffer. For example, preferably, a dispersion method, such as ultrasonic treatment, is used for dispersion. There is no limitation on the cleaning buffer, for example, Tris(hydroxymethyl)aminomethane buffer, glycin amide buffer or arginine buffer of specified concentration regulated to pH in a range from 8 to 9 can be used. For example, the pH of the cleaning buffer can be regulated by using hydrochloric acid, sodium hydroxide, etc. If needed, the cleaning treatment of the marked antibody 150 can be repeated multiple times.

(Storage Treatment)

During storage treatment, storage buffer is added into the marked antibody 150 separated out by the solid-liquid separation method, and the marked antibody 150 is uniformly dispersed into the storage buffer. For example, preferably, a dispersion method, such as ultrasonic treatment, is used for dispersion. For example, as the storage buffer, a solution which is prepared by adding anticoagulant and/or stabilizer of specified concentration into the cleaning buffer can be used. For example, as the anticoagulant, saccharides represented by sucrose, maltose, lactose and trehalose or polyhydric alcohols represented by glycerol and polyvinyl alcohol can be used. There is no limitation on the stabilizer, for example, protein, such as bovine serum albumin, ovalbumin, casein or gelatin, can be used. The storage treatment of the marked antibody 150 can be carried out in this way.

In each above-mentioned step, if needed, surfactant or preservative, such as sodium azide or paraben, can be used,

[Analyte Assay and Quantification Kit]

The analyte measurement kit in an embodiment of the present invention is a kit which is used to assay or quantify the analyte 160 contained in the sample by using the test strip 200 for lateral flow chromatography according to the method for measuring analyte in the present embodiment.

The kit of the present embodiment comprises:

the test strip 200 for lateral flow chromatography, comprising the membrane 110 and the determination portion 130 formed by immobilizing the capturing ligands specifically bound with the analyte 160 on the membrane 110; and an assay reagent, comprising the marked antibody 150 formed by utilizing the resin-metal composite 100 having the structure formed by immobilizing the plurality of metal particles 20 on the resin particle 10 to mark an antibody specifically bound with the analyte 160. If needed, the kit of the present embodiment can further comprise other components.

When the kit of the present invention is in use, after Step (I) is implemented by making the analyte 160 in the sample contact with the marked antibody 150 in the assay reagent, the sample is supplied to the reaction portion or sample addition portion 120 of the test strip 200, and Step (II) and Step (III) are then sequentially implemented. Or the assay reagent can be applied further upstream than the determination portion 130 of the test strip 200, it is suitable to add the sample on the formed reaction portion or place further upstream than the reaction portion (e.g. the sample addition portion 120) after the reaction portion is formed by drying, and Step (I) to Step (III) are then sequentially implemented.

Embodiment

The present invention is then described in detail in reference to embodiments, however, the present invention is not limited by these embodiments. In the following embodiments and comparative examples, various determinations and evaluations are based on the following way, unless otherwise indicated.

<Determination of Absorbance of Resin-Metal Composite>

With regard to the absorbance of the resin-metal composite, resin-metal composite dispersion (dispersion medium: water) prepared to 0.01 wt % is added into an optical whiteboard glass unit (the optical path length is 10 mm), and an instant multi-metering system (produced by Otsuka Electronics Co., Ltd., MCPD-3700) is used to determine absorbance of 570 nm in the case of gold. In the case of gold, absorbance in 570 nm which is 0.9 or more is set as ○ (Good), absorbance in 570 nm which is 0.5 to less than 0.9 is set as Δ (Acceptable), and absorbance in 570 nm which is less than 0.5 is set as × (Unacceptable).

<Solid Component Concentration Determination and Carried Metal Amount Determination>

1 g of dispersion before concentration regulation is added into a magnetic crucible, and is treated by heat under 70° C. for 3 hours. Weights before and after heat treatment are determined, and solid component concentration is worked out by the following formula.

solid component concentration (wt %)=[weight after drying (g)/weight before drying (g)]×100%

In addition, under 500° C., the sample treated by heat is further treated by heat for 5 hours, weights before and after heat treatment are determined, and the carried metal amount is worked out by the following formula.

carried metal amount (wt %)=[weight after heat treatment under 500° C. (g)/weight before heat treatment under 500° C. (g)]×100%

<Determination of Average Particle Sizes of Resin Particles and Resin-Metal Composite>

A disc centrifuge type particle size distribution determination device (CPS Disc Centrifuge DC24000 UHR, produced by CPS instruments, Inc.) is used for determination. Determination is carried out in the state of the resin-metal composite dispersed in water.

<Evaluation Utilizing Immunochromatography>

Determination utilizing immunochromatography shown hereinafter is carried out by using resin-metal composite-marked antibody dispersion prepared in each embodiment, and the performance of the resin-metal composite dispersion is evaluated.

(Evaluation Method)

Evaluation is carried out by using a monochrome screen for influenza A evaluation (produced by Adtec company), and coloration levels after 5 minutes, 10 minutes and 15 minutes are compared. In performance evaluation, two-fold dilution (1 to 1024 folds) of an influenza A positive control (APC) (the concentration of virus before APC dilution is 5000 FFU/ml) is used as an antigen.

(Evaluation Procedure)

3 μl of resin-metal composite-marked antibody dispersion is added into each well of a 96-well plate, and 100 μl of two-fold dilution (1 to 1024 folds) of the APC and 100 μl of negative control are mixed. Afterwards, 50 μl is added into the monochrome screen for influenza A evaluation, and coloration levels after 5 minutes, 10 minutes and 15 minutes are evaluated. A color sample for colloidal gold determination (produced by Adtec company) is used to determine the coloration levels.

<Determination of Average Particle Size of Metal Particles>

The determination of the average particle size of the metal particles means the determination of the surface mean diameter of the metal particles according to an image of a substrate produced by dripping the resin-metal composite dispersion into metallic meshes with carbon supporting membranes observed by a field emission scanning electron microscope (FE-SEM; produced by Hitachi High-Technologies, SU-9000).

Embodiment 1

<Synthesis of Resin Particles>

After ALIQUAT® 336 (tricaprylylmethylammonium chloride) [produced by Aldrich company] (1.00 g) and poly(ethylene glycol) methyl ether methacrylate (PEGMA, 2.00 g) are dissolved into 80 g of pure water, 2-vinylpyridine (2-VP, 9.90 g) and divinyl benzene (DVB, 0.100 g) are added, and under nitrogen flow, agitation is performed at 250 rpm under 60° C. for 30 minutes. After agitation, 2,2'-azobis (2-methylpropionamidine) dihydrochloride (AIBA, 0.100 g) dissolved in 9.00 g of pure water is dripped for 5 minutes, and is agitated at 250 rpm under 60° C. for 6 hours, and thereby resin particles, the average particle size of which is 0.45 μm, are obtained. The resin particles are precipitated by centrifugal separation (9000 rpm, 10 minutes), supernatant is removed, the resin particles are then dispersed in pure water again, and thereby 10 wt % resin particle dispersion is obtained.

<Synthesis of Resin-Metal Composite>

Figure 3:
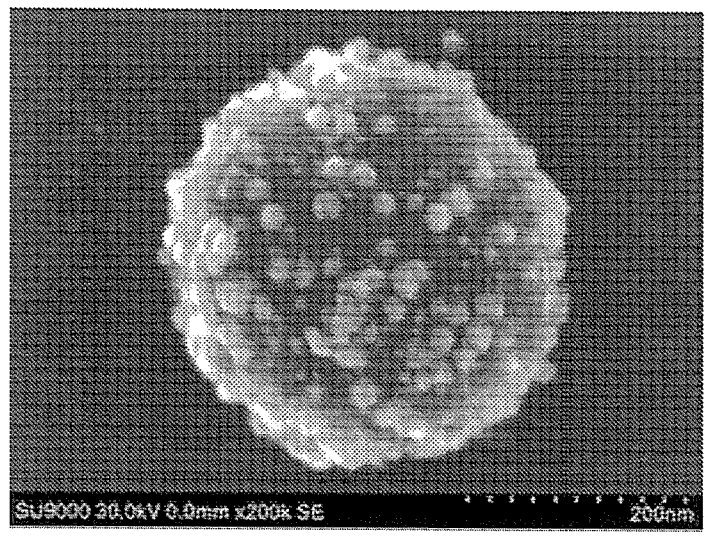
FIG. 3 is a scanning electron microscope (SEM) picture of a resin-gold composite obtained in embodiment 1.

30 mM aqueous chloroauric acid solution (80 g) is added into the resin particle dispersion (3.05 g), and is left alone under room temperature for 24 hours. Afterwards, the resin particles are precipitated by centrifugal separation (3000 rpm, 10 minutes), supernatant is removed, so that redundant chloroauric acid is removed, the resin particles are then dispersed into 55 g of pure water again, and thereby gold ion-adsorbing resin particle dispersion is prepared. After the gold ion-adsorbing resin particle dispersion (45 g) is dripped into 10 mM aqueous dimethylamine borane solution (450 ml) for 8 minutes, agitation is performed under room temperature for 2 hours, and thereby a resin-gold composite, the average particle size of which is 0.6 μm, is obtained. The resin-gold composite is precipitated by centrifugal separation (3000 rpm, 120 minutes), supernatant is removed, the resin-gold composite is then dispersed into 37 g of pure water again, an ultrafiltration membrane is used for refining, and thereby 1 wt % resin-gold composite dispersion is obtained. The result of absorbance of the resin-metal composite in the resin-gold composite dispersion determined according to the method is 1.20. In addition, the average particle size of the gold particles in the resin-metal composite is 22.0 nm, and the amount of carried gold is 49.4 wt %. The scanning electron microscope (SEM) picture of the prepared resin-gold composite is shown in FIG. 3.

Embodiment 2

Besides adding 10 mM aqueous chloroauric acid solution (56 g) into the resin particle dispersion (3.05 g) obtained in embodiment 1, by the same method as embodiment 1, gold ion-adsorbing resin particle dispersion, a resin-gold composite (average particle size: 0.6 μm) and 1 wt % resin-gold composite dispersion are obtained. The absorbance of the resin-gold composite in the resin-gold composite dispersion is 1.04. In addition, the average particle size of the gold particles in the resin-metal composite is 7.61 nm, and the amount of carried gold is 36.8 wt %.

Embodiment 3

<Synthesis of Resin Particles>

2-VP (9.90 g) and DVB (0.100 g) are added into 450 g of pure water, and under nitrogen flow, agitation is performed at 250 rpm under 60° C. for 30 minutes. After 30 minutes of agitation, AIBA (0.100 g) dissolved in 9.00 g of pure water is dripped for 5 minutes, agitation is performed at 250 rpm for 6 hours, and thereby resin particles, the average particle size of which is 0.10 μm, are obtained. The resin particles are precipitated by centrifugal separation (9000 rpm, 20 minutes), supernatant is removed, the resin particles are then dispersed in pure water again, and thereby 10 wt % resin particle dispersion is obtained.

<Synthesis of Resin-Metal Composite>

30 mM aqueous chloroauric acid solution (198 g) is added into the resin particle dispersion (5.0 g), and is left alone under room temperature for 24 hours. Afterwards, the resin particles are precipitated by centrifugal separation (3000 rpm, 10 minutes), supernatant is removed, so that redundant chloroauric acid is removed, the resin particles are then dispersed into 1.5 g of pure water again, and thereby gold ion-adsorbing resin particle dispersion is prepared. After the gold ion-adsorbing resin particle dispersion (1.5 g) is dripped into 10 mM aqueous dimethylamine borane solution (65 ml) for 2 minutes, agitation is performed under room temperature for 2 hours, and thereby a resin-gold composite, the average particle size of which is 0.22 μm, is obtained. After 10 wt % dispersion (BYK194) (600 μl) is added into the resin-gold composite and agitated for 1 hour, precipitation is performed by centrifugal separation (9000 rpm, 10 minutes), and supernatant is removed. Afterwards, an appropriate amount of pure water is added for dispersion again, an ultrafiltration membrane is used for refining, and thereby 1 wt % resin-gold composite dispersion is obtained. The absorbance of the resin-gold composite in the resin-gold composite dispersion is 1.12. In addition, the average particle size of the gold particles in the resin-metal composite is 22.6 nm, and the amount of carried gold is 37.0 wt %.

Comparative Example 1

<Immunochromatography Evaluation>

100 μg of influenza antibody is mixed into 1 ml (0.1 wt %) of coloring latex (produced by Merck Millipore company, coloring Estapor functional particle, K1030, average particle size: 392 nm, absorbance in 570 nm: 0.83, absorbance in 400 nm: 1.11), and is agitated under room temperature for about 3 hours, so that the coloring latex and the antibody are bound. Bovine serum albumin solution is added until final concentration is changed into 1%, and is agitated under room temperature for 2 hours to block the coloring latex. A coloring latex-marked antibody is prepared by recovery after 5 minutes of centrifugal separation at 12000 rpm under 4° C. and suspension in buffer containing 0.2% of bovine serum albumin.

The prepared coloring latex-marked antibody is used to carry out determination utilizing immunochromatography shown below, and the performance of the coloring latex is evaluated.

(Evaluation Method)

Evaluation is carried out by using the monochrome screen for influenza A evaluation (produced by Adtec company), and coloration levels after 5 minutes, 10 minutes and 15 minutes are compared. In performance evaluation, two-fold dilution (1 to 1024 folds) of an influenza A positive control (APC) (the concentration of virus before APC dilution is 5000 FFU/ml) is used as an antigen.

(Evaluation Procedure)

3 µl of coloring latex-marked antibody is added into each well of the 96-well plate, and 100 µl of two-fold dilution (1 to 1024 folds) of the APC and 100 µl of negative control are mixed. Afterwards, 50 µl is added into the monochrome screen for influenza A evaluation, and coloration levels after 5 minutes, 10 minutes and 15 minutes are evaluated. The result is represented below.

heating reflux device is used to boil the aqueous chloroauric acid solution as the aqueous chloroauric acid solution is violently agitated, 25 ml of 38.8 mM aqueous sodium citrate solution is added after boiling, and whether the solution is changed from light yellow to deep red is determined. After continuing to be heated for 10 minutes as the solution is agitated, the solution is agitated under room temperature for about 30 minutes and left alone to be cooled. A membrane filter, the pore diameter of which is 2 µm, is used to filter the solution, and the solution is transferred into a conical flask and stored in the shade. The average particle size of the prepared particles is 12.3 nm.

<Immunochromatography Evaluation>

100 µg of influenza antibody is mixed into 1 ml of obtained colloidal gold (OD=10), and is agitated under room temperature for about 3 hours, so that the colloidal gold is bound with the antibody. Bovine serum albumin solution is added until final concentration is changed into 1%, and is agitated under room temperature for 2 hours to block the surface of the colloidal gold. A colloidal gold-marked antibody is prepared by recovery after 5 minutes of centrifugal separation at 12000 rpm under 4° C. and suspension in buffer containing 0.2% of bovine serum albumin.

TABLE 1A

| Slot No. | | 1 | 2 | 3 | 4 | 5 | 6 | 7 | 8 | 9 | 10 | 11 | 12 |
|---|---|---|---|---|---|---|---|---|---|---|---|---|---|
| | | | | | | Coloring latex | | | | | | | |
| Antigen dilution | | APC × 1 | APC × 2 | APC × 4 | APC × 8 | APC × 16 | APC × 32 | APC × 64 | APC × 128 | APC × 256 | APC × 512 | APC × 1024 | Negative control |
| Coloration level | After 5 minutes | 3.5 | 2.0 | 1.0 | 0.5 | 0.1 | 0 | 0 | 0 | 0 | 0 | 0 | 0 |
| | After 10 minutes | 4.0 | 2.5 | 1.5 | 0.5 | 0.1 | 0.1 | 0 | 0 | 0 | 0 | 0 | 0 |
| | After 15 minutes | 4.5 | 3.5 | 2.5 | 1.0 | 0.5 | 0.1 | 0.1 | 0 | 0 | 0 | 0 | 0 |

According to Table 1A, it can be determined that the coloring latex-marked antibody shows good coloration for the antigen diluted 16 folds.

The results of absorbance of the above-mentioned embodiments and comparative examples are gathered and shown in Table 1B.

TABLE 1B

| | Embodiment 1 | Embodiment 2 | Embodiment 3 | Comparative Example 1 |
|---|---|---|---|---|
| Absorbance in 570 nm | 1.20 | 1.04 | 1.12 | 0.83 |
| Evaluation | ○ | ○ | ○ | Δ |

Comparative Example 2

<Synthesis of Colloidal Gold>

250 ml of 1 mM aqueous chloroauric acid solution is added into a 500 ml three-neck round-bottomed flask, a The prepared colloidal gold-marked antibody is used to carry out determination utilizing immunochromatography shown below, and the performance of the colloidal gold is evaluated.

(Evaluation Method)

Evaluation is carried out by using the monochrome screen for influenza A evaluation (produced by Adtec company), and coloration levels after 5 minutes, 10 minutes and 15 minutes are compared. In performance evaluation, two-fold dilution (1 to 1024 folds) of an influenza A positive control (APC) (the concentration of virus before APC dilution is 5000 FFU/ml) is used as an antigen.

(Evaluation Procedure)

3 µl of colloidal gold-marked antibody is added into each well of the 96-well plate, and 100 µl of two-fold dilution (1 to 1024 folds) of the APC and 100 µl of negative control are mixed. Afterwards, 50 µl is added into the monochrome screen for influenza A evaluation, and coloration levels after 5 minutes, 10 minutes and 15 minutes are evaluated. The result is represented below.

TABLE 2

| Slot No. | 1 | 2 | 3 | 4 | 5 | 6 | 7 | 8 | 9 | 10 | 11 | 12 |
|---|---|---|---|---|---|---|---|---|---|---|---|---|
| | | | | | Colloidal gold | | | | | | | |
| Antigen dilution | APC × 1 | APC × 2 | APC × 4 | APC × 8 | APC × 16 | APC × 32 | APC × 64 | APC × 128 | APC × 256 | APC × 512 | APC × 1024 | Negative control |

TABLE 2-continued

| Slot No. | | 1 | 2 | 3 | 4 | 5 | 6 | 7 | 8 | 9 | 10 | 11 | 12 |
|---|---|---|---|---|---|---|---|---|---|---|---|---|---|
| | | | | | | Colloidal gold | | | | | | | |
| Coloration level | After 5 minutes | 4.0 | 3.0 | 2.0 | 1.5 | 0.5 | 0.1 | 0 | 0 | 0 | 0 | 0 | 0 |
| | After 10 minutes | 4.5 | 3.5 | 2.5 | 2.0 | 1.0 | 0.5 | 0.1 | 0 | 0 | 0 | 0 | 0 |
| | After 15 minutes | 5.0 | 4.5 | 3.5 | 3.0 | 2.0 | 1.0 | 0.1 | 0.1 | 0 | 0 | 0 | 0 |

According to Table 2, it can be determined that the colloidal gold-marked antibody shows good coloration for the antigen diluted 32 folds.

Comparative Example 3

<Synthesis of Resin Particles>

After ALIQUAT® 336 (tricaprylylmethylammonium chloride) [produced by Aldrich company] (5.00 g) and poly(ethylene glycol) methyl ether methacrylate (PEGMA, 10.00 g) are dissolved into 389.5 g of pure water, 2-vinylpyridine (2-VP, 48.00 g) and divinyl benzene (DVB, 2.00 g) are added, and under nitrogen flow, agitation is performed at 150 rpm under 30° C. for 50 minutes, and is then performed under 60° C. for 30 minutes. After agitation, 2,2'-azobis(2-methylpropionamidine) dihydrochloride (AIBA, 0.500 g) dissolved in 50.00 g of pure water is dripped for 2 minutes, and is agitated at 150 rpm under 60° C. for 3.5 hours, and thereby resin particles, the average particle size of which is 200 nm, are obtained. The resin particles are precipitated by centrifugal separation (9000 rpm, 60 minutes), supernatant is removed, the resin particles are dispersed into pure water again, and after this operation is performed three times, impurities are removed by dialysis. Afterwards, concentration is regulated, and thereby 10 wt % resin particle dispersion is obtained.

After 1233 ml of pure water is added into the resin beads (50 ml), 30 mM aqueous chloroauric acid solution (100 ml) is added, and the resin beads are kept under room temperature for 24 hours. Afterwards, the resin particles are precipitated by centrifugal separation (3100 rpm, 30 minutes), supernatant is removed, this operation is repeated three times, and thereby redundant chloroauric acid is removed. Afterwards, concentration is regulated, and thereby 2.5 wt % gold ion-adsorbing resin particle dispersion is prepared.

2.5 wt % gold ion-adsorbing resin particle dispersion (42.4 ml) is then added into 1580 ml of pure water, the mixed solution of 528 mM aqueous dimethylamine borane solution (10 ml) and 528 mM aqueous boric acid solution (10 ml) is dripped for 4 minutes as agitation is performed at 160 rpm under 20° C., agitation is then performed under room temperature for 2 hours, and thereby a resin-gold composite, the average particle size of which is 250 nm, is obtained. The resin-gold composite is precipitated by centrifugal separation (3100 rpm, 60 minutes), supernatant is removed, the resin-gold composite is dispersed into pure water again, this operation is repeated three times, refining and concentration regulation are performed by dialysis, and thereby 1 wt % resin-gold composite dispersion is obtained. The result of absorbance of the prepared resin-gold composite determined according to the method is 1.69. In addition, the average particle size of the formed gold particles is 75.0 nm, and the amount of carried gold is 52.3 wt %.

<Immunochromatography Evaluation>

100 μg of influenza antibody is mixed into 1 ml of obtained resin-gold composite dispersion (0.1 wt %), and agitation is performed under room temperature for about 3 hours, so that the resin-gold composite is bound with the antibody. Bovine serum albumin solution is added until final concentration is changed into 1%, and agitation is performed under room temperature for 2 hours to block the surface of the resin-gold composite. Resin-gold composite-marked antibody dispersion is prepared by recovery after 5 minutes of centrifugal separation at 12000 rpm under 4° C. and suspension in buffer containing 0.2% of bovine serum albumin.

Determination utilizing immunochromatography is carried out by using the prepared resin-gold composite-marked antibody dispersion, and the performance of the resin-gold composite dispersion is evaluated. The result is represented below.

TABLE 3

| Slot No. | | 1 | 2 | 3 | 4 | 5 | 6 | 7 | 8 | 9 | 10 | 11 | 12 |
|---|---|---|---|---|---|---|---|---|---|---|---|---|---|
| Antigen dilution | | APC × 1 | APC × 2 | APC × 4 | APC × 8 | APC × 16 | APC × 32 | APC × 64 | APC × 128 | APC × 256 | APC × 512 | APC × 1024 | Negative control |
| Coloration level | After 5 minutes | 5.0 | 3.0 | 2.0 | 1.0 | 0.1 | 0 | 0 | 0 | 0 | 0 | 0 | 0 |
| | After 10 minutes | 5.5 | 4.0 | 3.0 | 1.0 | 0.5 | 0.1 | 0 | 0 | 0 | 0 | 0 | 0 |
| | After 15 minutes | 5.5 | 4.5 | 4.0 | 3.5 | 1.0 | 0.1 | 0 | 0 | 0 | 0 | 0 | 0 |

According to Table 3, it can be determined that the resin-gold composite-marked antibody shows good coloration for the antigen diluted 16 folds.

Embodiment 4

After ALIQUAT® 336 (tricaprylylmethylammonium chloride) [produced by Aldrich company] (1.00 g) and poly(ethylene glycol) methyl ether methacrylate (PEGMA, 10.00 g) are dissolved into 300 g of pure water, 2-vinylpyridine (2-VP, 48.00 g) and divinyl benzene (DVB, 2.00 g) are added, and under nitrogen flow, agitation is performed at 150 rpm under 30° C. for 50 minutes, and is then performed under 60° C. for 30 minutes. After agitation, 2,2'-azobis(2-methylpropionamidine) dihydrochloride (AIBA, 0.500 g) dissolved in 18.00 g of pure water is dripped for 0.5 minutes, and is agitated at 150 rpm under 60° C. for 3.5 hours, and thereby resin particles, the average particle size of which is 500 nm, are obtained. The resin particles are precipitated by centrifugal separation (9000 rpm, 40 minutes), supernatant is removed, the resin particles are dispersed into pure water again, and after this operation is performed three times, impurities are removed by dialysis. Afterwards, concentration is regulated, and thereby 10 wt % resin particle dispersion is obtained.

After 1233 ml of pure water is added into the resin beads (50 ml), 30 mM aqueous chloroauric acid solution (100 ml) is added, and the resin beads are kept under room temperature for 24 hours. Afterwards, the resin particles are precipitated by centrifugal separation (3100 rpm, 30 minutes), supernatant is removed, this operation is repeated three times, and thereby redundant chloroauric acid is removed. Afterwards, concentration is regulated, and thereby 2.5 wt % gold ion-adsorbing resin particle dispersion is prepared.

2.5 wt % gold ion-adsorbing resin particle dispersion (42.4 ml) is then added into 1580 ml of pure water, 528 mM aqueous dimethylamine borane solution (10 ml) is dripped for 2 minutes as agitation is performed at 160 rpm under 20° C., agitation is then performed under room temperature for 2 hours, and thereby resin-gold composite, the average particle size of which is 510 nm, is obtained. The resin-gold composite is precipitated by centrifugal separation (3100 rpm, 60 minutes), supernatant is removed, the resin-gold composite is dispersed into pure water again, this operation is repeated three times, refining and concentration regulation are performed by dialysis, and thereby 1 wt % resin-gold composite dispersion is obtained. The result of absorbance of the prepared resin-gold composite determined according to the method is 1.01. In addition, the average particle size of the formed gold particles is 46.3 nm, and the amount of carried gold is 54.2 wt %. In the resin-gold composite, the gold particles include encased gold particles completely encased in the resin particle, partially exposed gold particles having a portion embedded in the resin particle and a portion exposed from the resin particle, and surface-adsorbed gold particles absorbed on the surface of the resin particle, and at least portions of the gold particles are three-dimensionally distributed on the surface section of the resin particle.

<Immunochromatography Evaluation>

100 μg of influenza antibody is mixed into 1 ml of obtained resin-gold composite dispersion (0.1 wt %), and agitation is performed under room temperature for about 3 hours, so that the resin-gold composite is bound with the antibody. Bovine serum albumin solution is added until final concentration is changed into 1%, and agitation is performed under room temperature for 2 hours to block the surface of the resin-gold composite. Resin-gold composite-marked antibody dispersion is prepared by recovery after 5 minutes of centrifugal separation at 12000 rpm under 4° C. and suspension in buffer containing 0.2% of bovine serum albumin.

Determination utilizing immunochromatography is carried out by using the prepared resin-gold composite-marked antibody dispersion, and the performance of the resin-gold composite dispersion is evaluated. The result is represented below.

TABLE 4

| Slot No. | | 1 | 2 | 3 | 4 | 5 | 6 | 7 | 8 | 9 | 10 | 11 | 12 |
|---|---|---|---|---|---|---|---|---|---|---|---|---|---|
| Antigen dilution | | APC × 1 | APC × 2 | APC × 4 | APC × 8 | APC × 16 | APC × 32 | APC × 64 | APC × 128 | APC × 256 | APC × 512 | APC × 1024 | Negative control |
| Coloration level | After 5 minutes | 5.0 | 4.5 | 3.5 | 3.0 | 2.5 | 1.5 | 1.0 | 0.5 | 0.1 | 0.1 | 0 | 0 |
| | After 10 minutes | 6.0 | 5.5 | 4.5 | 4.0 | 3.5 | 2.5 | 2.0 | 1.0 | 0.5 | 0.1 | 0 | 0 |
| | After 15 minutes | 7.0 | 6.5 | 5.5 | 4.5 | 4.0 | 3.0 | 2.0 | 1.0 | 0.5 | 0.1 | 0.1 | 0 |

According to Table 4, it can be determined that the resin-gold composite-marked antibody shows good coloration for the antigen diluted 256 folds.

Embodiment 5

Embodiment 5

After ALIQUAT® 336 (tricaprylylmethylammonium chloride) [produced by Aldrich company] (0.50 g) and poly(ethylene glycol) methyl ether methacrylate (PEGMA, 10.00 g) are dissolved into 300 g of pure water, 2-vinylpyridine (2-VP, 48.00 g) and divinyl benzene (DVB, 2.00 g) are added, and under nitrogen flow, agitation is performed at 150 rpm under 30° C. for 50 minutes, and is then performed under 60° C. for 30 minutes. After agitation, 2,2'-azobis(2-methylpropionamidine) dihydrochloride (AIBA, 0.500 g) dissolved in 18.00 g of pure water is dripped for 0.5 minutes, and agitation is performed at 150 rpm under 60° C. for 3.5 hours, and thereby resin particles, the average particle size of which is 613 nm, are obtained. The resin particles are precipitated by centrifugal separation (9000 rpm, 40 minutes), supernatant is removed, the resin particles are dispersed into pure water again, and after this operation is performed three times, impurities are removed by dialysis. Afterwards, concentration is regulated, and thereby 10 wt % resin particle dispersion is obtained.

After 1233 ml of pure water is added into the resin beads (50 ml), 30 mM aqueous chloroauric acid solution (100 ml) is added, and the resin beads are kept under room temperature for 24 hours. Afterwards, the resin particles are precipitated by centrifugal separation (3100 rpm, 30 minutes), supernatant is removed, this operation is repeated three times, and thereby redundant chloroauric acid is removed. Afterwards, concentration is regulated, and thereby 2.5 wt % gold ion-adsorbing resin particle dispersion is prepared.

2.5 wt % gold ion-adsorbing resin particle dispersion (42.4 ml) is then added into 1580 ml of pure water, 528 mM aqueous dimethylamine borane solution (10 ml) is dripped for 2 minutes as agitation is performed at 160 rpm under 3° C., agitation is then performed under room temperature for 2 hours, and thereby resin-gold composite, the average particle size of which is 625 nm, is obtained. The resin-gold composite is precipitated by centrifugal separation (3100 rpm, 60 minutes), supernatant is removed, the resin-gold composite is dispersed into pure water again, this operation is repeated three times, refining and concentration regulation are performed by dialysis, and thereby 1 wt % resin-gold composite dispersion is obtained. The result of absorbance of the prepared resin-gold composite dispersion determined according to the method is 0.98. In addition, the average particle size of the formed gold particles is 25.0 nm, and the amount of carried gold is 55.3 wt %. In the resin-gold composite, the gold particles include encased gold particles completely encased in the resin particle, partially exposed gold particles having a portion embedded in the resin particle and a portion exposed from the resin particle, and surface-adsorbed gold particles absorbed on the surface of the resin particle, and at least portions of the gold particles are three-dimensionally distributed on the surface section of the resin particle.

<Immunochromatography Evaluation>

100 μg of influenza antibody is mixed into 1 ml of obtained resin-gold composite dispersion (0.1 wt %), and agitation is performed under room temperature for about 3 hours, so that the resin-gold composite is bound with the antibody. Bovine serum albumin solution is added until final concentration is changed into 1%, and agitation is performed under room temperature for 2 hours to block the surface of the resin-gold composite. Resin-gold composite-marked antibody dispersion is prepared by recovery after 5 minutes of centrifugal separation at 12000 rpm under 4° C. and suspension in buffer containing 0.2% of bovine serum albumin.

Determination utilizing immunochromatography is carried out by using the prepared resin-gold composite-marked antibody dispersion, and the performance of the resin-gold composite dispersion is evaluated. The result is represented below.

TABLE 5

| Slot No. | | 1 | 2 | 3 | 4 | 5 | 6 | 7 | 8 | 9 | 10 | 11 | 12 |
|---|---|---|---|---|---|---|---|---|---|---|---|---|---|
| Antigen dilution | | APC × 1 | APC × 2 | APC × 4 | APC × 8 | APC × 16 | APC × 32 | APC × 64 | APC × 128 | APC × 256 | APC × 512 | APC × 1024 | Negative control |
| Coloration level | After 5 minutes | 5.0 | 4.5 | 3.5 | 3.0 | 2.5 | 1.5 | 1.0 | 0.5 | 0.5 | 0.1 | 0 | 0 |
| | After 10 minutes | 6.0 | 5.5 | 4.5 | 4.0 | 3.5 | 2.5 | 2.0 | 1.0 | 0.5 | 0.1 | 0.1 | 0 |
| | After 15 minutes | 7.0 | 6.5 | 5.5 | 4.5 | 4.0 | 3.0 | 2.0 | 1.0 | 0.5 | 0.1 | 0.1 | 0 |

According to Table 5, it can be determined that the resin-gold composite-marked antibody shows good coloration for the antigen diluted 256 folds.

Embodiment 6

After ALIQUAT® 336 (tricaprylylmethylammonium chloride) [produced by Aldrich company] (1.00 g) and poly(ethylene glycol) methyl ether methacrylate (PEGMA, 10.00 g) are dissolved into 300 g of pure water, 4-vinylpyridine (4-VP, 48.00 g) and divinyl benzene (DVB, 2.00 g) are added, and under nitrogen flow, agitation is performed at 150 rpm under 30° C. for 50 minutes, and is then performed under 60° C. for 30 minutes. After agitation, 2,2'-azobis(2-methylpropionamidine) dihydrochloride (AIBA, 0.500 g) dissolved in 18.00 g of pure water is dripped for 2 minutes, and is agitated at 150 rpm under 60° C. for 3.5 hours, and thereby resin particles, the average particle size of which is 438 nm, are obtained. The resin particles are precipitated by centrifugal separation (9000 rpm, 45 minutes), supernatant is removed, the resin particles are dispersed into pure water again, and after this operation is performed three times, impurities are removed by dialysis. Afterwards, concentration is regulated, and thereby 10 wt % resin particle dispersion is obtained.

After 1233 ml of pure water is added into the resin beads (50 ml), 30 mM aqueous chloroauric acid solution (100 ml) is added, and the resin beads are kept under room temperature for 24 hours. Afterwards, the resin particles are precipitated by centrifugal separation (3100 rpm, 30 minutes), supernatant is removed, this operation is repeated three times, and thereby redundant chloroauric acid is removed. Afterwards, concentration is regulated, and thereby 2.5 wt % gold ion-adsorbing resin particle dispersion is prepared.

2.5 wt % gold ion-adsorbing resin particle dispersion (42.4 ml) is then added into 1580 ml of pure water, 528 mM aqueous dimethylamine borane solution (10 ml) is dripped for 2 minutes as agitation is performed at 160 rpm under 3° C., agitation is then performed under room temperature for 2 hours, and thereby resin-gold composite, the average particle size of which is 448 nm, is obtained. The resin-gold composite is precipitated by centrifugal separation (3100 rpm, 60 minutes), supernatant is removed, the resin-gold composite is dispersed into pure water again, this operation is repeated three times, refining and concentration regulation are performed by dialysis, and thereby 1 wt % resin-gold composite dispersion is obtained. The result of absorbance of the prepared resin-gold composite dispersion determined according to the method is 0.99. In addition, the average particle size of the formed gold particles is 24.0 nm, and the amount of carried gold is 55.7 wt %. In the resin-gold composite, the gold particles include encased gold particles completely encased in the resin particle, partially exposed gold particles having a portion embedded in the resin particle and a portion exposed from the resin particle, and surface-adsorbed gold particles absorbed on the surface of the resin particle, and at least portions of the gold particles are three-dimensionally distributed on the surface section of the resin particle.

<Immunochromatography Evaluation>

100 μg of influenza antibody is mixed into 1 ml of obtained resin-gold composite dispersion (0.1 wt %), and agitation is performed under room temperature for about 3 hours, so that the resin-gold composite is bound with the antibody. Bovine serum albumin solution is added until final concentration is changed into 1%, and agitation is performed under room temperature for 2 hours to block the surface of the resin-gold composite. Resin-gold composite-marked antibody dispersion is prepared by recovery after 5 minutes of centrifugal separation at 12000 rpm under 4° C. and suspension in buffer containing 0.2% of bovine serum albumin.

Determination utilizing immunochromatography is carried out by using the prepared resin-gold composite-marked antibody dispersion, and the performance of the resin-gold composite dispersion is evaluated. The result is represented below.

TABLE 6

| Slot No. | | 1 | 2 | 3 | 4 | 5 | 6 | 7 | 8 | 9 | 10 | 11 | 12 |
|---|---|---|---|---|---|---|---|---|---|---|---|---|---|
| Antigen dilution | | APC × 1 | APC × 2 | APC × 4 | APC × 8 | APC × 16 | APC × 32 | APC × 64 | APC × 128 | APC × 256 | APC × 512 | APC × 1024 | Negative control |
| Coloration level | After 5 minutes | 5.0 | 4.5 | 3.5 | 3.0 | 2.5 | 1.5 | 1.0 | 0.5 | 0.1 | 0 | 0 | 0 |
| | After 10 minutes | 6.0 | 5.5 | 4.5 | 4.0 | 3.5 | 2.5 | 2.0 | 1.0 | 0.5 | 0.1 | 0 | 0 |
| | After 15 minutes | 7.0 | 6.5 | 5.5 | 4.5 | 4.0 | 3.0 | 2.0 | 1.0 | 0.5 | 0.1 | 0.1 | 0 |

According to Table 6, it can be determined that the resin-gold composite-marked antibody shows good coloration for the antigen diluted 256 folds.

Embodiment 7

After ALIQUAT® 336 (tricaprylylmethylammonium chloride) [produced by Aldrich company] (1.00 g) and poly(ethylene glycol) methyl ether methacrylate (PEGMA, 10.00 g) are dissolved into 300 g of pure water, 3-vinylpyridine (3-VP, 48.00 g) and divinyl benzene (DVB, 2.00 g) are added, and under nitrogen flow, agitation is performed at 150 rpm under 30° C. for 50 minutes, and is then performed under 60° C. for 30 minutes. After agitation, 2,2'-azobis(2-methylpropionamidine) dihydrochloride (AIBA, 0.500 g) dissolved in 18.00 g of pure water is dripped for 2 minutes, and is agitated at 150 rpm under 60° C. for 3.5 hours, and thereby resin particles, the average particle size of which is 429 nm, are obtained. The resin particles are precipitated by centrifugal separation (9000 rpm, 45 minutes), supernatant is removed, the resin particles are dispersed into pure water again, and after this operation is performed three times, impurities are removed by dialysis. Afterwards, concentration is regulated, and thereby 10 wt % resin particle dispersion is obtained.

After 1233 ml of pure water is added into the resin beads (50 ml), 30 mM aqueous chloroauric acid solution (100 ml) is added, and the resin beads are kept under room temperature for 24 hours. Afterwards, the resin particles are precipitated by centrifugal separation (3100 rpm, 30 minutes), supernatant is removed, this operation is repeated three times, and thereby redundant chloroauric acid is removed. Afterwards, concentration is regulated, and thereby 2.5 wt % gold ion-adsorbing resin particle dispersion is prepared.

2.5 wt % gold ion-adsorbing resin particle dispersion (42.4 ml) is then added into 1580 ml of pure water, 528 mM aqueous dimethylamine borane solution (10 ml) is dripped for 2 minutes as agitation is performed at 160 rpm under 3° C., agitation is then performed under room temperature for 2 hours, and thereby resin-gold composite, the average particle size of which is 436 nm, is obtained. The resin-gold composite is precipitated by centrifugal separation (3100 rpm, 60 minutes), supernatant is removed, the resin-gold composite is dispersed into pure water again, this operation is repeated three times, refining and concentration regulation are performed by dialysis, and thereby 1 wt % resin-gold composite dispersion is obtained. The result of absorbance of the prepared resin-gold composite dispersion determined according to the method is 1.03. In addition, the average particle size of the formed gold particles is 24.3 nm, and the amount of carried gold is 55.5 wt %. In the resin-gold composite, the gold particles include encased gold particles completely encased in the resin particle, partially exposed gold particles having a portion embedded in the resin particle and a portion exposed from the resin particle, and surface-adsorbed gold particles absorbed on the surface of the resin particle, and at least portions of the gold particles are three-dimensionally distributed on the surface section of the resin particle.

<Immunochromatography Evaluation>

100 μg of influenza antibody is mixed into 1 ml of obtained resin-gold composite dispersion (0.1 wt %), and agitation is performed under room temperature for about 3 hours, so that the resin-gold composite is bound with the antibody. Bovine serum albumin solution is added until final concentration is changed into 1%, and agitation is performed under room temperature for 2 hours to block the surface of the resin-gold composite. Resin-gold composite-marked antibody dispersion is prepared by recovery after 5 minutes of centrifugal separation at 12000 rpm under 4° C. and suspension in buffer containing 0.2% of bovine serum albumin.

Determination utilizing immunochromatography is carried out by using the prepared resin-gold composite-marked antibody dispersion, and the performance of the resin-gold composite dispersion is evaluated. The result is represented below.

TABLE 7

| Slot No. | | 1 | 2 | 3 | 4 | 5 | 6 | 7 | 8 | 9 | 10 | 11 | 12 |
|---|---|---|---|---|---|---|---|---|---|---|---|---|---|
| Antigen dilution | | APC × 1 | APC × 2 | APC × 4 | APC × 8 | APC × 16 | APC × 32 | APC × 64 | APC × 128 | APC × 256 | APC × 512 | APC × 1024 | Negative control |
| Coloration level | After 5 minutes | 5.0 | 4.5 | 3.5 | 3.0 | 2.5 | 1.5 | 1.0 | 0.5 | 0.1 | 0 | 0 | 0 |
| | After 10 minutes | 6.0 | 5.5 | 4.5 | 4.0 | 3.5 | 2.5 | 2.0 | 0.5 | 0.1 | 0 | 0 | 0 |
| | After 15 minutes | 7.0 | 6.5 | 5.5 | 4.5 | 4.0 | 3.0 | 2.0 | 1.0 | 0.5 | 0.1 | 0 | 0 |

According to Table 7, it can be determined that the resin-gold composite-marked antibody shows good coloration for the antigen diluted 256 folds.

Embodiment 8

After 2-(Diisopropylamino)ethyl methacrylate (DPA, 10.3 g), poly(propylene glycol)diacrylate (0.2 g) and poly(ethylene glycol) methyl ether methacrylate (PEGMA, 2.0 g) are dissolved into 85 g of pure water, and under nitrogen flow, agitation is performed at 150 rpm under 30° C. for 50 minutes, and is then carried out under 70° C. for 30 minutes. After agitation, ammonium persulphate (APS, 0.10 g) dissolved in 2.00 g of pure water is dripped for 2 minutes, and is agitated at 150 rpm under 70° C. for 3.5 hours, and thereby resin particles, the average particle size of which is 338 nm, are obtained. The resin particles are precipitated by centrifugal separation (9000 rpm, 45 minutes), supernatant is removed, the resin particles are dispersed into pure water again, and after this operation is performed three times, impurities are removed by dialysis. Afterwards, concentration is regulated, and thereby 10 wt % resin particle dispersion is obtained.

After 1233 ml of pure water is added into the resin beads (50 ml), 30 mM aqueous chloroauric acid solution (100 ml) is added, and the resin beads are kept under room temperature for 24 hours. Afterwards, the resin particles are precipitated by centrifugal separation (3100 rpm, 30 minutes), supernatant is removed, this operation is repeated three times, and thereby redundant chloroauric acid is removed. Afterwards, concentration is regulated, and thereby 2.5 wt % gold ion-adsorbing resin particle dispersion is prepared.

2.5 wt % gold ion-adsorbing resin particle dispersion (42.4 ml) is then added into 1580 ml of pure water, 528 mM aqueous dimethylamine borane solution (10 ml) is dripped for 2 minutes as agitation is performed at 160 rpm under 3° C., agitation is then performed under room temperature for 2 hours, and thereby a resin-gold composite, the average particle size of which is 345 nm, is obtained. The resin-gold composite is precipitated by centrifugal separation (3100 rpm, 60 minutes), supernatant is removed, the resin-gold composite is dispersed into pure water again, this operation is repeated three times, refining and concentration regulation are performed by dialysis, and thereby 1 wt % resin-gold composite dispersion is obtained. The result of absorbance of the prepared resin-gold composite dispersion determined according to the method is 0.96. In addition, the average particle size of the formed gold particles is 24.6 nm, and the amount of carried gold is 48.5 wt %. In the resin-gold composite, the gold particles include encased gold particles completely encased in the resin particle, partially exposed gold particles having a portion embedded in the resin particle and a portion exposed from the resin particle, and surface-adsorbed gold particles absorbed on the surface of the resin particle, and at least portions of the gold particles are three-dimensionally distributed on the surface section of the resin particle.

<Immunochromatography Evaluation>

100 μg of influenza antibody is mixed into 1 ml of obtained resin-gold composite dispersion (0.1 wt %), and agitation is performed under room temperature for about 3 hours, so that the resin-gold composite is bound with the antibody. Bovine serum albumin solution is added until final concentration is changed into 1%, and is agitated under room temperature for 2 hours to block the surface of the resin-gold composite. Resin-gold composite-marked antibody dispersion is prepared by recovery after 5 minutes of centrifugal separation at 12000 rpm under 4° C. and suspension in buffer containing 0.2% of bovine serum albumin.

Determination utilizing immunochromatography is carried out by using the prepared resin-gold composite-marked antibody dispersion, and the performance of the resin-gold composite dispersion is evaluated. The result is represented below.

TABLE 8

| Slot No. | | 1 | 2 | 3 | 4 | 5 | 6 | 7 | 8 | 9 | 10 | 11 | 12 |
|---|---|---|---|---|---|---|---|---|---|---|---|---|---|
| Antigen dilution | | APC × 1 | APC × 2 | APC × 4 | APC × 8 | APC × 16 | APC × 32 | APC × 64 | APC × 128 | APC × 256 | APC × 512 | APC × 1024 | Negative control |
| Coloration level | After 5 minutes | 4.0 | 3.0 | 2.5 | 2.0 | 1.5 | 1.0 | 0.5 | 0.1 | 0 | 0 | 0 | 0 |
| | After 10 minutes | 5.0 | 4.0 | 3.5 | 3.0 | 2.5 | 2.0 | 1.0 | 0.5 | 0.1 | 0.1 | 0 | 0 |
| | After 15 minutes | 6.0 | 5.0 | 4.0 | 3.5 | 3.0 | 2.5 | 1.5 | 1.0 | 0.5 | 0.1 | 0 | 0 |

According to Table 8, it can be determined that the resin-gold composite-marked antibody shows good coloration for the antigen diluted 256 folds.

Embodiment 9

<Synthesis of Resin Particles>

After ALIQUAT® 336 (tricaprylylmethylammonium chloride) [produced by Aldrich company] (3.00 g) and poly(ethylene glycol) methyl ether methacrylate (PEGMA, 10.00 g) are dissolved into 300 g of pure water, 2-vinylpyridine (2-VP, 49.50 g) and divinyl benzene (DVB, 0.50 g) are added, and under nitrogen flow, agitation is performed at 150 rpm under 30° C. for 50 minutes, and is then performed under 60° C. for 30 minutes. After agitation, 2,2'-azobis(2-methylpropionamidine) dihydrochloride (AIBA, 0.250 g) dissolved in 18.00 g of pure water is dripped for 2 minutes, agitation is performed at 150 rpm under 60° C. for 3.5 hours, and thereby resin particles, the average particle size of which is 370 nm, are obtained. The resin particles are precipitated by centrifugal separation (9000 rpm, 60 minutes), supernatant is removed, the resin particles are dispersed into pure water again, and after this operation is performed three times, impurities are removed by dialysis. Afterwards, concentration is regulated, and thereby 10 wt % resin particle dispersion is obtained.

After 1233 ml of pure water is added into the resin beads (50 ml), 30 mM aqueous chloroauric acid solution (100 ml) is added, and the resin beads are kept under room temperature for 24 hours. Afterwards, the resin particles are precipitated by centrifugal separation (3100 rpm, 30 minutes), supernatant is removed, this operation is repeated three times, and thereby redundant chloroauric acid is removed.

Afterwards, concentration is regulated, and thereby 2.5 wt % gold ion-adsorbing resin particle dispersion is prepared.

Figure 4:
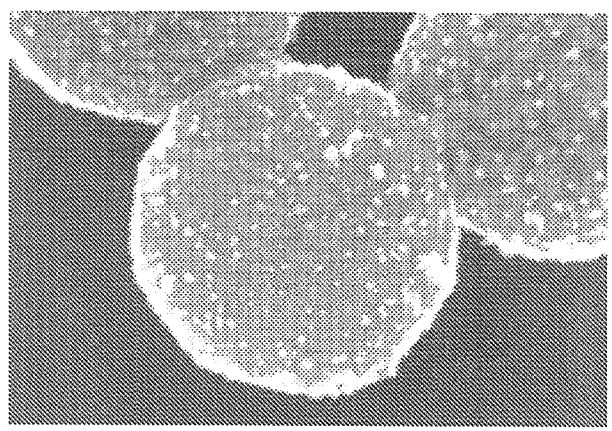
FIG. 4 is a scanning electron microscope (SEM) picture of a resin-gold composite obtained in embodiment 9.
Figure 5:
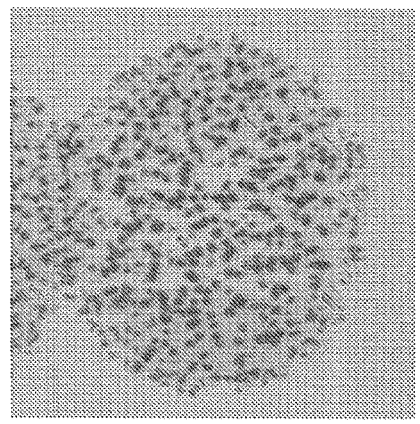
FIG. 5 is a scanning transmission electron microscope (STEM) picture of the section of the resin-gold composite obtained in embodiment 9.

2.5 wt % gold ion-adsorbing resin particle dispersion (42.4 ml) is then added into 1580 ml of pure water, 528 mM aqueous dimethylamine borane solution (10 ml) is dripped for 2 minutes as agitation is performed at 160 rpm under 20° C., agitation is then performed under room temperature for 2 hours, and thereby resin-gold composite, the average particle size of which is 393 nm, is obtained. The resin-gold composite is precipitated by centrifugal separation (3100 rpm, 60 minutes), supernatant is removed, the resin-gold composite is dispersed into pure water again, this operation is repeated three times, refining and concentration regulation are performed by dialysis, and thereby 1 wt % resin-gold composite dispersion is obtained. The result of absorbance of the prepared resin-gold composite dispersion determined according to the method is 0.92. In addition, the average particle size of the formed gold particles is 14.9 nm, and the amount of carried gold is 55.8 wt %. The scanning electron microscope (SEM) picture of the surface of the obtained resin-gold composite is shown in FIG. 4, and the scanning transmission electron microscope (STEM) picture of its section is shown in FIG. 5 In the resin-gold composite, the gold particles include encased gold particles completely encased in the resin particle, partially exposed gold particles having a portion embedded in the resin particle and a portion exposed from the resin particle, and surface-adsorbed gold particles absorbed on the surface of the resin particle, and at least portions of the gold particles are three-dimensionally distributed on the surface section of the resin particle.

<Immunochromatography Evaluation>

100 μg of influenza antibody is mixed into 1 ml of obtained resin-gold composite dispersion (0.1 wt %), and agitation is performed under room temperature for about 3 hours, so that the resin-gold composite is bound with the antibody. Bovine serum albumin solution is added until final concentration is changed into 1%, and agitation is performed under room temperature for 2 hours to block the surface of the resin-gold composite. Resin-gold composite-marked antibody dispersion is prepared by recovery after 5 minutes of centrifugal separation at 12000 rpm under 4° C. and suspension in buffer containing 0.2% of bovine serum albumin.

Determination utilizing immunochromatography is carried out by using the prepared resin-gold composite-marked antibody dispersion, and the performance of the resin-gold composite dispersion is evaluated. The result is represented below.

Embodiment 10

<Synthesis of Resin Particles>

After ALIQUAT® 336 (tricaprylylmethylammonium chloride) [produced by Aldrich company] (2.00 g) and poly(ethylene glycol) methyl ether methacrylate (PEGMA, 10.00 g) are dissolved into 300 g of pure water, 2-vinylpyridine (2-VP, 48.00 g) and divinyl benzene (DVB, 2.00 g) are added, and under nitrogen flow, agitation is performed at 150 rpm under 30° C. for 50 minutes, and is then performed under 60° C. for 30 minutes. After agitation, 2,2'-azobis(2-methylpropionamidine) dihydrochloride (AIBA, 0.500 g) dissolved in 18.00 g of pure water is dripped for 2 minutes, and is agitated at 150 rpm under 60° C. for 3.5 hours, and thereby resin particles, the average particle size of which is 380 nm, are obtained. The resin particles are precipitated by centrifugal separation (9000 rpm, 60 minutes), supernatant is removed, the resin particles are dispersed into pure water again, and after this operation is performed three times, impurities are removed by dialysis. Afterwards, concentration is regulated, and thereby 10 wt % resin particle dispersion is obtained.

After 1233 ml of pure water is added into the resin beads (50 ml), 30 mM aqueous chloroauric acid solution (100 ml) is added, and the resin beads are kept under room temperature for 24 hours. Afterwards, the resin particles are precipitated by centrifugal separation (3100 rpm, 30 minutes), supernatant is removed, this operation is repeated three times, and thereby redundant chloroauric acid is removed. Afterwards, concentration is regulated, and thereby 2.5 wt % gold ion-adsorbing resin particle dispersion is prepared.

Figure 6:
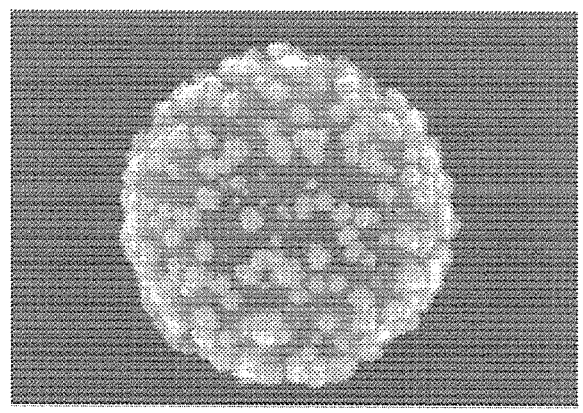
FIG. 6 is a scanning electron microscope (SEM) picture of a resin-gold composite obtained in embodiment 10.

2.5 wt % gold ion-adsorbing resin particle dispersion (42.4 ml) is then added into 1580 ml of pure water, 528 mM aqueous dimethylamine borane solution (10 ml) is dripped for 2 minutes as agitation is performed at 160 rpm under 20° C., agitation is then performed under room temperature for 2 hours, and thereby resin-gold composite, the average particle size of which is 399 nm, is obtained. The resin-gold composite is precipitated by centrifugal separation (3100 rpm, 60 minutes), supernatant is removed, the resin-gold composite is dispersed into pure water again, this operation is repeated three times, refining and concentration regulation are performed by dialysis, and thereby 1 wt % resin-gold composite dispersion is obtained. The result of absorbance of the prepared resin-gold composite dispersion determined according to the method is 0.96. In addition, the average particle size of the formed gold particles is 25.0 nm, and the amount of carried gold is 53.2 wt %. The scanning electron microscope (SEM) picture of the surface of the obtained resin-gold composite is shown in FIG. 6, and the scanning

TABLE 9

| Slot No. | | 1 | 2 | 3 | 4 | 5 | 6 | 7 | 8 | 9 | 10 | 11 | 12 |
|---|---|---|---|---|---|---|---|---|---|---|---|---|---|
| Antigen dilution | | APC × 1 | APC × 2 | APC × 4 | APC × 8 | APC × 16 | APC × 32 | APC × 64 | APC × 128 | APC × 256 | APC × 512 | APC × 1024 | Negative control |
| Coloration level | After 5 minutes | 4.0 | 3.0 | 1.0 | 0.5 | 0.1 | 0 | 0 | 0 | 0 | 0 | 0 | 0 |
| | After 10 minutes | 4.5 | 3.5 | 2.0 | 1.5 | 1.0 | 0.5 | 0.1 | 0 | 0 | 0 | 0 | 0 |
| | After 15 minutes | 5.0 | 4.0 | 3.0 | 2.5 | 2.0 | 1.0 | 0.5 | 0.1 | 0 | 0 | 0 | 0 |

Figure 7:
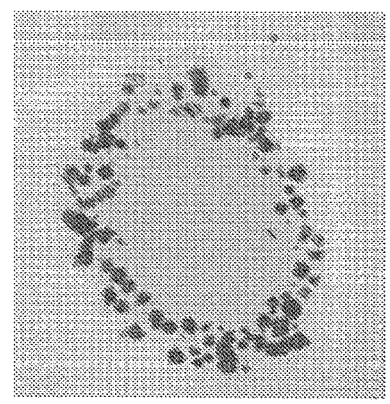
FIG. 7 is a scanning transmission electron microscope (STEM) picture of the section of the resin-gold composite obtained in embodiment 10.

According to Table 9, it can be determined that the resin-gold composite-marked antibody shows good coloration for the antigen diluted 64 folds.

transmission electron microscope (STEM) picture of its section is shown in FIG. 7 In the resin-gold composite, the gold particles include encased gold particles completely encased in the resin particle, partially exposed gold particles having a portion embedded in the resin particle and a portion exposed from the resin particle, and surface-adsorbed gold particles absorbed on the surface of the resin particle, and at least portions of the gold particles are three-dimensionally distributed on the surface section of the resin particle.

<Immunochromatography Evaluation>

100 μg of influenza antibody is mixed into 1 ml of obtained resin-gold composite dispersion (0.1 wt %), and agitation is performed under room temperature for about 3 hours, so that the resin-gold composite is bound with the antibody. Bovine serum albumin solution is added until final concentration is changed into 1%, and agitation is performed under room temperature for 2 hours to block the surface of the resin-gold composite. Resin-gold composite-marked antibody dispersion is prepared by recovery after 5 minutes of centrifugal separation at 12000 rpm under 4° C. and suspension in buffer containing 0.2% of bovine serum albumin.

Determination utilizing immunochromatography is carried out by using the prepared resin-gold composite-marked antibody dispersion, and the performance of the resin-gold composite dispersion is evaluated. The result is represented below.

is removed, the resin particles are then dispersed in pure water again, and thereby 2.1 wt % resin particle dispersion B-1 is obtained.

<Synthesis of Resin-Gold Composite>

30 mM aqueous chloroauric acid solution (106.6 g) is added into B-1 (19.09 g), and is left alone under room temperature for 24 hours. Afterwards, the resin particles are precipitated by centrifugal separation (3000 rpm, 10 minutes), supernatant is removed, so that redundant chloroauric acid is removed, the resin particles are then dispersed into 40 g of pure water again, and thereby gold ion-adsorbing resin particle dispersion C-1 is prepared. After C-1 (20 g) is dripped into 3.3 mM aqueous dimethylamine borane solution (600 ml) for 4 minutes, agitation is performed under 8° C. for 1 hour, and is then performed under room temperature for 5 hours, and thereby resin-gold composite D-1, the average particle size of which is 0.38 μm, is obtained. D-1 is precipitated by centrifugal separation (3000 rpm, 120 minutes), supernatant is removed, an appropriate amount of pure water is then added for dispersion again, an ultrafiltration membrane is then used for refining, and thereby 1 wt % resin-gold composite dispersion E-1 is obtained. The result of absorbance of the resin-gold composite F-1 in E-1 determined according to the method is 1.0. In addition, the

TABLE 10

| Slot No. | | 1 | 2 | 3 | 4 | 5 | 6 | 7 | 8 | 9 | 10 | 11 | 12 |
|---|---|---|---|---|---|---|---|---|---|---|---|---|---|
| Antigen dilution | | APC × 1 | APC × 2 | APC × 4 | APC × 8 | APC × 16 | APC × 32 | APC × 64 | APC × 128 | APC × 256 | APC × 512 | APC × 1024 | Negative control |
| Coloration level | After 5 minutes | 4.5 | 4.0 | 3.5 | 3.0 | 2.5 | 1.5 | 1.0 | 0.5 | 0.1 | 0 | 0 | 0 |
| | After 10 minutes | 5.5 | 5.0 | 4.5 | 4.0 | 3.5 | 2.5 | 1.5 | 0.5 | 0.5 | 0.1 | 0 | 0 |
| | After 15 minutes | 6.5 | 5.5 | 5.0 | 4.5 | 4.0 | 3.0 | 1.5 | 1.0 | 0.5 | 0.1 | 0 | 0 |

According to Table 10, it can be determined that the resin-gold composite-marked antibody shows good coloration for the antigen diluted 256 folds.

If the section image of FIG. 5 of embodiment 9 and the section image of FIG. 7 of embodiment 10 are compared, then the assay sensitivity of immunochromatography of embodiment 10 in which 60% to 100%, preferably 75% to 100%, of the gold particles exist in a range of 50% of particle radius in a depth direction from the surface of the resin particle is more excellent.

EXPERIMENTAL EXAMPLES RELATED TO PREPARATION OF MARKED ANTIBODY

Preparation Example 1

<Synthesis of Resin Particles>

After ALIQUAT® 336 (tricaprylylmethylammonium chloride) [produced by Aldrich company] (1.00 g) and poly(ethylene glycol) methyl ether methacrylate (PEGMA, 2.00 g) are dissolved into 80 g of pure water, 2-vinylpyridine (2-VP, 9.90 g) and divinyl benzene (DVB, 0.100 g) are added, and under nitrogen flow, agitation is performed at 250 rpm under 60° C. for 30 minutes. After agitation, 2,2'-azobis (2-methylpropionamidine) dihydrochloride (AIBA, 0.100 g) dissolved in 9.00 g of pure water is dripped for 5 minutes, and is agitated at 250 rpm under 60° C. for 6 hours, and thereby resin particles A-1, the average particle size of which is 0.36 μm, are obtained. A-1 is precipitated by centrifugal separation (9000 rpm, 10 minutes), supernatant average particle size of the gold particles in F-1 is 22.0 nm, and the amount of carried gold is 49.1 wt %.

[Reagents]

In the experimental examples and reference experimental examples, the following reagents and so on are used.

Anti-influenza A monoclonal antibody (7.15 mg/mL/PBS): Produced by Adtec Co., Ltd.

Binding buffer a: 100 mM Utilizing HCl to regulate boric acid solution into pH≈93

Binding buffer b: 100 mM Utilizing HCl to regulate boric acid solution into pH≈4

Binding buffer c: 100 mM Utilizing HCl to regulate boric acid solution into pH≈5

Binding buffer d: 100 mM Boric acid solution pH≈6.5

Binding buffer e: 100 mM Utilizing NaCl to regulate boric acid solution into pH≈7.5.

Binding buffer f: 100 mM Utilizing NaCl to regulate boric acid solution into pH≈8.5.

Binding buffer g: 50 mM 2-morpholinoethanesulfonic acid solution pH 3.8

Blocking buffer a: Utilizing HCl to regulate 1 wt % bovine serum albumin solution into pH≈5.

Blocking buffer b: Utilizing HCl to regulate 1 wt % bovine serum albumin solution into pH≈7.

Blocking buffer c: Utilizing HCl to regulate 1 wt % bovine serum albumin solution into pH≈8.5.

Blocking buffer d: Utilizing HCl to regulate 1 wt % bovine serum albumin solution into pH≈9.5.

Cleaning buffer: Utilizing HCl to regulate 5 mM Tris (hydroxymethyl)aminomethane solution into pH≈8.5.

Storage buffer: Adding sucrose into cleaning buffer until concentration is changed into 10 wt %.

Influenza A positive control (APC): Prepared by using sample treatment solution (produced by Adtec Co., Ltd.) to dilute an influenza A virus passivation antigen (produced by Adtec Co., Ltd.) 100 folds. The antigen concentration of the APC is equivalent to 5000 FFU/ml.

Negative control: Sample treatment solution (produced by Adtec Co., Ltd.)

AuNCP beads: Resin-gold composite (1 wt %; average particle size: 380 nm) obtained in preparation example 1

Experimental Example 1

(Binding Step)

0.1 mL of AuNCP beads as resin-metal composite are put into microtubes [IBIS (registered trademark; produced by AS ONE company) 2 mL], and 0.9 mL of binding buffer a is added. After upside-down mixing for sufficient mixing, 100 μg of anti-influenza A monoclonal antibody 100 is added, moreover, upside-down agitation is performed under room temperature for 3 hours, and thereby marked antibody-containing solution A-1 which contains the anti-influenza A monoclonal antibody marked by utilizing the resin-metal composite is obtained.

(Blocking Step)

Afterwards, after the marked antibody-containing solution A-1 is cooled by ice bath, centrifugal separation is performed at 12000 rpm for 5 minutes, supernatant is removed, 1 mL of blocking buffer a is then added into solid component residue, ultrasonic dispersion treatment is performed for 10 to 20 seconds, further, upside-down agitation is performed under room temperature for 2 hours, and thereby marked antibody-containing solution B-1 is obtained.

(Cleaning Treatment)

Afterwards, after the marked antibody-containing solution B-1 is cooled by ice bath, centrifugal separation is performed at 12000 rpm for 5 minutes, supernatant is removed, 1 mL of cleaning buffer is then added into solid component residue, and ultrasonic dispersion treatment is performed for 10 to 20 seconds. This operation is repeated three times as cleaning treatment.

(Storage Treatment)

Afterwards, after ice bath cooling, centrifugal separation is performed at 12000 rpm for 5 minutes, supernatant is removed, 1 mL of storage buffer is then added into solid component residue, ultrasonic dispersion treatment is performed for 10 to 20 seconds, and thereby marked antibody-containing solution C-1 is obtained.

Experimental Example 2

Binding buffer b is used to substitute for binding buffer a in the binding step of experimental example 1, and besides, marked antibody-containing solution A-2, marked antibody-containing solution B-2 and marked antibody-containing solution C-2 are obtained in the same way as experimental example 1.

Experimental Example 3

Binding buffer c is used to substitute for binding buffer a in the binding step of experimental example 1, and besides, marked antibody-containing solution A-3, marked antibody-containing solution B-3 and marked antibody-containing solution C-3 are obtained in the same way as experimental example 1.

Experimental Example 4

Binding buffer d is used to substitute for binding buffer a in the binding step of experimental example 1, and besides, marked antibody-containing solution A-4, marked antibody-containing solution B-4 and marked antibody-containing solution C-4 are obtained in the same way as experimental example 1.

Reference Experimental Example 1

When binding buffer e is used to substitute for binding buffer a in the binding step of experimental example 1, resin-metal composite is aggregated, so it is hard to obtain marked antibody-containing solution.

Reference Experimental Example 2

When binding buffer f is used to substitute for binding buffer a in the binding step of experimental example 1, a resin-metal composite is aggregated, so it is hard to obtain marked antibody-containing solution.

Experimental Example 5

Blocking buffer b is used to substitute for the blocking buffer a in the blocking step of experimental example 1, and besides, marked antibody-containing solution B-5 and marked antibody-containing solution C-5 are obtained in the same way as experimental example 1.

Experimental Example 6

Blocking buffer c is used to substitute for the blocking buffer a in the blocking step of experimental example 1, and besides, marked antibody-containing solution B-6 and marked antibody-containing solution C-6 are obtained in the same way as experimental example 1.

Reference Experimental Example 3

As the result of using blocking buffer d to substitute for the blocking buffer a in the blocking step of experimental example 1, the marked antibody after the binding step shows good dispersibility, however, after the blocking step, marked antibody is aggregated, so it is hard to obtain marked antibody-containing solution.

Experimental Example 7

Binding buffer g is used to substitute for binding buffer a in the binding step of experimental example 1, and besides, marked antibody-containing solution A-7, marked antibody-containing solution B-7 and marked antibody-containing solution C-7 are obtained in the same way as experimental example 1.

<Evaluation Method>

Evaluation is carried out by using the monochrome screen for influenza A evaluation (produced by Adtec company), and coloration levels after 5 minutes, 10 minutes and 15 minutes are compared. A color sample for colloidal gold determination (produced by Adtec company) is used to determine the coloration levels. In screening and evaluation, antigen uses an influenza A positive control (APC). In performance evaluation, antigen uses 2-fold dilution (1- to 1024-fold dilution) of the APC.

<Screening and Evaluation>

3 μL of marked antibody-containing solution C-1, 34 μL of marked antibody-containing solution C-2, 3 μL of marked antibody-containing solution C-3, 3 μL of marked antibody-containing solution C-4, 3 μL of marked antibody-containing solution C-5, 3 μL of marked antibody-containing solution C-6 and 3 μL of marked antibody-containing solution C-7 which are obtained in experimental example 1 to experimental example 7 are respectively added into seven wells of the 96-well plate, and 100 μL of APC is mixed into each well. Afterwards, 50 μL is added into the monochrome screen for influenza A evaluation, and coloration levels after 5 minutes, 10 minutes and 15 minutes are evaluated. The result is shown in Table 11. Moreover, the higher the values in Table 11 are, the higher coloration levels are (intenser coloration).

TABLE 11

|  |  | Marked antibody-containing solution | | | | | | |
|---|---|---|---|---|---|---|---|---|
|  |  | C-1 | C-2 | C-3 | C-4 | C-5 | C-6 | C-7 |
| Coloration level | After 5 minutes | 6.5 | 6.0 | 6.0 | 5.5 | 5.0 | 4.0 | 4.0 |
|  | After 10 minutes | 7.0 | 6.0 | 6.0 | 6.0 | 6.5 | 5.5 | 5.0 |
|  | After 15 minutes | 7.0 | 6.5 | 7.0 | 6.5 | 7.0 | 6.0 | 5.0 |

According to Table 11, it can be determined that the marked antibody-containing solution C-1 obtained in experimental example 1 shows the strongest coloration, having excellent marking performance.

<Performance Evaluation>

3 μL of marked antibody-containing solution C-1 obtained in experimental example 1 is added into each of 12 wells of the 96-well plate, and 100 μL of 2-fold dilution (1- to 1024-fold dilution, respectively represented as APC×1 to APC×1024) of the APC and 100 μL of negative control are mixed. Afterwards, 50 μL is added into the monochrome screen for influenza A evaluation, and coloration levels after 5 minutes, 10 minutes and 15 minutes are evaluated. The result is shown in Table 12. Moreover, the higher the values in Table 12 are, the higher coloration levels are (intenser coloration).

TABLE 12

|  |  | Marked antibody-containing solution C-1 | | | | | | | | | | | |
|---|---|---|---|---|---|---|---|---|---|---|---|---|---|
| Antigen dilution |  | APC × 1 | APC × 2 | APC × 4 | APC × 8 | APC × 16 | APC × 32 | APC × 64 | APC × 128 | APC × 256 | APC × 512 | APC × 1024 | Negative control |
| Coloration level | After 5 minutes | 6.0 | 5.0 | 4.0 | 3.5 | 3.0 | 1.5 | 1.0 | 0.5 | 0.1 | 0 | 0 | 0 |
|  | After 10 minutes | 7.0 | 6.0 | 5.0 | 4.5 | 4.0 | 3.0 | 2.0 | 1.0 | 0.5 | 0 | 0 | 0 |
|  | After 15 minutes | 7.5 | 6.5 | 5.5 | 5.0 | 4.5 | 3.5 | 2.5 | 1.5 | 1.0 | 0.1 | 0 | 0 |

According to Table 12, it can be determined that the marked antibody-containing solution C-1 obtained in experimental example 1 shows good coloration for the antigen diluted 256 folds, having excellent marking performance.

The embodiments of the present invention are elaborated above with the illustrated purposes, however, the present invention is not limited by the embodiments.

The present international application claims the priority of Japanese Patent Application No. 2014-136356 applied on Jul. 1, 2014, and Japanese Patent Application No. 2014-136357 applied on Jul. 1, 2014, and all the contents of these present applications are integrated into this case.

LIST OF REFERENCE NUMERALS

10: Resin particle
20: Metal particle
30: Encased metal particle
40: Partially exposed metal particle
50: Surface-adsorbed metal particle
60: Surface layer part
100: Resin-metal composite
110: Membrane
120: Sample addition portion
130: Determination portion
131: Capturing ligand
140: Liquid-absorbing portion
150: Marked antibody
160: Analyte
170: Composite
200: Test strip

What is claimed is:

1. A marker, comprising a resin-gold composite with a structure formed by immobilizing old particles on a resin particle, characterized by
having
the average particle size of the resin-gold composite being in a range of 300 nm to 1000 nm;
the average particle size of the gold particles being in a range of 20 nm to 70 nm;
wherein the gold particles comprise
a first portion of the gold particles completely encased in the resin particle,
a second portion of the gold particles having a part embedded in the resin particle and another part exposed from the resin particle, and
a remaining portion of the gold particles adsorbed on the surface of the resin particle;
wherein 75% to 100% of the gold particles exist in a range of 50% of particle radius in a depth direction from a surface of the resin particle;
wherein the resin particle comprises a nitrogenous polymer having nitrogen ions on the main chain or the side chain, and the nitrogenous polymer is selected from the group consisting of poly-2-vinylpyridine, poly-3-vinylpyridine, poly-4-vinylpyridine and 2-(diisopropylamino)ethyl methacrylate.

2. The marker according to claim 1, wherein the resin-gold composite is dispersed in water.

3. The marker according to claim 1, wherein the marker is used in adsorbing an antigen or an antibody on the surface of the resin-gold composite.

4. An immunoassay method, characterized by using the marker according to claim 1.

5. An immunoassay reagent, comprising the marker according to claim 1.

6. A method for measuring analyte, assaying or quantifying an analyte contained in a sample, characterized by
using a lateral-flow chromatographic test strip comprising a membrane and a determination portion formed by immobilizing capturing ligands specifically bound with the analyte on the membrane to carry out steps including step (I) to step (II) hereinafter:
step (I): step of making the analyte contained in the sample contact with a marked antibody formed by utilizing the marker according to claim 1 to mark an antibody specifically bound with the analyte;
step (II): step of making the composite containing the analyte and the marked antibody formed in step (I) contact with the capturing ligands in the determination portion; and
step (III): step of determining colored intensity derived from the localized surface plasmon resonance of the resin-gold composite in the marker.

7. An analyte measurement kit, using a lateral-flow chromatographic test strip, used to assay or quantify an analyte contained in a sample, used to assay or quantify the analyte, and the analyte measurement kit comprising:
the lateral-flow chromatographic test strip, comprising a membrane and a determination portion formed by immobilizing capturing ligands specifically bound with the analyte on the membrane; and
an assay reagent, containing a marked antibody formed by utilizing the marker according to claim 1 to mark an antibody specifically bound with the analyte.

8. A lateral-flow chromatographic test strip, used to assay or quantify an analyte contained in a sample, comprising
a membrane;
a determination portion, formed by immobilizing capturing ligands specifically bound with the analyte on the membrane in the spreading direction of a sample; and
a reaction portion, comprising a marked antibody formed by utilizing the marker according to claim 1 to mark an antibody specifically bound with the analyte further upstream than the determination portion.

* * * * *